United States Patent [19]

Clemens et al.

[11] Patent Number: 5,478,857

[45] Date of Patent: Dec. 26, 1995

[54] USE OF PLA$_2$ INHIBITORS AS TREATMENT FOR ALZHEIMER'S DISEASE

[75] Inventors: James A. Clemens, Indianapolis, Ind.; Michael J. Sofia, Lawrenceville, N.J.; Diane T. Stephenson, Indianapolis, Ind.

[73] Assignee: Eli Lilly and Company, Indianapolis, Ind.

[21] Appl. No.: 173,544

[22] Filed: Dec. 23, 1993

[51] Int. Cl.$^6$ .................. A61K 31/41; A61K 31/35; A61K 31/335; A61K 31/19; A61K 31/165

[52] U.S. Cl. .................. 514/381; 514/454; 514/455; 514/456; 514/457; 514/458; 514/568; 514/570; 514/571; 514/622

[58] Field of Search .................. 514/381, 454, 514/455, 456, 457, 458, 568, 570, 571, 622

[56] References Cited

U.S. PATENT DOCUMENTS 4,814,339  3/1989  Rotondo .................. 514/332

Primary Examiner—Kimberly R. Jordan
Attorney, Agent, or Firm—Paul J. Gaylo; David E. Boone

[57] ABSTRACT

This invention provides methods for the treatment or prevention of Alzheimer's disease in a mammal which comprises administering to a mammal in need thereof an effective amount of an inhibitor of phospholipase A$_2$. This invention also provides a series of compounds which are useful as inhibitors of phospholipases A$_2$, especially cytosolic phospholipase A$_2$.

12 Claims, No Drawings

USE OF PLA₂ INHIBITORS AS TREATMENT FOR ALZHEIMER'S DISEASE

BACKGROUND OF THE INVENTION

Alzheimer's disease is a degenerative disorder of the human brain. Clinically, it appears as a progressive dementia. Its histopathology is characterized by degeneration of neurons, gliosis, and the abnormal deposition of proteins in the brain. Pathological hallmarks include neurofibrillary tangles (paired helical filaments) and amyloid deposits within the parenchyma and cerebral vasculature.

While there is no general agreement as to the chemical nature of neurofibrillary tangles, the major constituent of both the amyloid plaque cores and the amyloid of the congophilic angiopathy has been shown to be a 4500 Dalton protein originally termed β-protein or amyloid A4. Throughout this document this protein is referred to as β-amyloid peptide or protein.

β-amyloid peptide is proteolytically derived from a transmembrane protein, the amyloid precursor protein. Different splice forms of the amyloid precursor protein are encoded by a widely expressed gene. see, e.g., K. Beyreuther and B. Müller-Hill, *Annual Reviews in Biochemistry*, 58:287–307 (1989). β-amyloid peptide consists, in its longest forms, of 42 or 43 amino acid residues. J. Kang, et al., *Nature* (London), 325:733–736 (1987). These peptides, however, vary as to their amino-termini. C. Hilbich, et al., *Journal of Molecular Biology*, 18:149–163 (1991).

Because senile plaques are invariably surrounded by dystrophic neurites, it was proposed early that β-amyloid peptide is involved in the loss of neuronal cells that occurs in Alzheimer's disease. B. Yankner and co-workers were the first to demonstrate that synthetic β-amyloid peptide could be neurotoxic in vitro and in vivo. B. A. Yankner, et al., *Science*, 245:417 (1989; See, also, N. W. Kowall, et al., *Proceedings of the National Academy of Sciences, U.S.A.*, 88:7247 (1991). Other research groups, however, were unable to consistently demonstrate direct toxicity with β-amyloid peptide. See, e.g., *Neurobiology of Aging*, 13:535 (K. Kosik and P. Coleman, eds. 1992). Even groups receiving β-amyloid peptide from a common source demonstrate conflicting results. D. Price, et al., *Neurobiology of Aging*, 13:623–625 (1991)(and the references cited therein).

Because of the debilitating effects of Alzheimer's disease there continues to exist a need for effective treatments. This invention provides methods for the treatment of Alzheimer's disease in mammals.

Recent studies have begun to indicate that a major component of the pathology of Alzheimer's disease is chronic inflammation. See, J. Schnabel, *Science*, 260:1719–1720 (1993). Indeed, pathological investigations have demonstrated the presence of glial hyperactivity, acute phase proteins, and complement factors within affected areas of the brains of persons affected with Alzheimer's disease. Administration of nonsteroidal anti-inflammatory drugs appears to slow the advance of Alzheimer's disease. Id. Understanding this inflammatory component of Alzheimer's disease, therefore, will lead to advances in novel methods of treating patients suffering from this disease.

Inflammatory disorders account for a significant number of debilitating diseases. Inflammatory states, such as arthritis, psoriasis, asthma, and possibly atherosclerosis, stem from inflammatory reactions in the joints, skin, and blood vessels. It is generally believed that a central role in the inflammatory reaction is the production of phospholipid metabolites called eicosanoids. The eicosanoids represent a family of important mediators such as the leukotrienes, prostaglandins, lipoxins, hydroxyeicosatetranoic acid, and thromboxanes. It is believed that the generation of eicosanoids is dependent on the availability of arachidonic acid which is liberated from phospholipids by the action of phospholipase $A_2$ (EC 3.1.1.4).

Phospholipase $A_2$ (PLA₂) is the common name for phosphatide 2-acylhydrolase, which catalyzes the hydrolysis of the sn-2-acyl ester bond of phosphoglycerides which results in the production of equimolar amounts of lysophospholipids and free fatty acids. see, E. A. Dennis, "*The Enzymes*", Vol. 16, Academic Press, New York, (1983). Phospholipase $A_2$ enzymes are found in all living species and form a diverse family of enzymes. Over forty phospholipase $A_2$ enzymes have been structurally characterized, and they show a high degree of sequence homology. J. Chang, et al., *Biochemical Pharmacology*, 36:2429–2436, (1987).

The best characterized varieties of PLA₂ enzyme are the secreted forms, which are released into the extracellular environment where they aid in the digestion of biological materials. The secreted forms have a molecular weight of about 12–15,000 (Chang, et al, supra). In contrast, cytosolic phospholipases $A_2$ are found in small amounts within the cell and play a key role in the biosynthetic pathway leading to the formation of the platelet activating factors and the eicosanoids. D. Mobilio and L. A. Marshall, *Annual Reports in Medicinal Chemistry*, 24; 157–166, (1989).

The cytosolic phospholipases $A_2$ have a molecular weight of approximately 85,000 daltons. J. D. Clark, et al., *Cell*, 65:1043–1051 (1991). Free arachidonic acid is the rate limiting precursor for the production of eicosanoids and is liberated from its membrane phospholipid store by the action of cytosolic PLA₂. E. A. Dennis, *Drug Development and Research*, 10:205–220, (1987). The same enzymatic step also produces lysophospholipids which may be converted to platelet-activating factors. Thus, it is believed that cytosolic PLA₂ is central to the regulation of the biosynthetic pathways of potent lipid mediators of inflammation.

Due to the central role in the inflammatory component of Alzheimer's disease that appears to be played by cytosolic phospholipase $A_2$, it is desirable to identify and characterize new inhibitors of this enzyme.

SUMMARY OF THE INVENTION

The present invention describes a method for the treatment or prevention of Alzheimer's disease in a mammal which comprises administering to a mammal in need of said treatment an effective amount of an inhibitor of phospholipase $A_2$ activity or a pharmaceutically acceptable salt of said inhibitor.

The present invention also describes a method for the treatment or prevention of Alzheimer's disease in a mammal which comprises administering to a mammal in need of said treatment an effective amount of a compound of Formula I

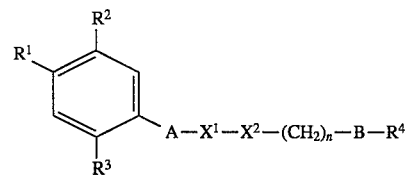

wherein $R^1$ is hydrogen, $C_1$-$C_6$ alkoxycarbonyl, $C_1$-$C_6$ alkoxy, $C_2$-$C_6$ alkanoyl, $C_1$-$C_6$ alkyl, or phenyl, said phenyl being optionally substituted with one or more halo substituents;

$R^2$ is hydroxy, $C_1$-$C_6$ alkoxy, hydrogen, or $C_1$-$C_6$ alkyl;

$R^3$ is $C_1$-$C_6$ alkyl or hydrogen;

A is —O— or —$CH_2$—;

$X^1$ and $X^2$ are each —$CH_2$— or taken together form —CH=CH—;

n is 0 to 6;

B is —O—, —$CH_2$—, or —$C(R^5R^6)$—;

where $R^5$ and $R^6$ are independently $C_1$-$C_6$ alkyl;

$R^4$ is phenyl, xanthenyl, tetrazolyl, or 3,4-dihydrobenzopyranyl, said phenyl, xanthenyl, or 3,4-dihydrobenzopyranyl being optionally substituted with one or more substituents selected from the group consisting of $C_1$-$C_6$ alkyl, $C_1$-$C_6$ alkoxy, oxo, carboxy, $C_1$-$C_6$ alkoxycarbonyl, carboxy-($C_1$-$C_6$ alkoxy)-, carboxy-($C_1$-$C_6$ alkyl)-, $NR^7R^8$—C (O)—($C_1$-$C_6$ alkyl)-,

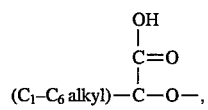

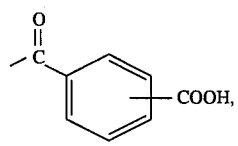

and

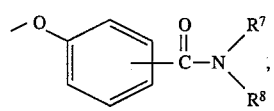

where $R^7$ and $R^8$ are independently hydrogen, $C_1$-$C_6$ alkyl, $C_1$-$C_6$ alkylsulfonyl, or phenylsulfonyl; or a pharmaceutically acceptable salt thereof.

In another embodiment this invention provides a method for the treatment or prevention of a condition associated with an excess of phospholipase $A_2$ activity which comprises administering to a mammal in need thereof an effective amount of a compound of Formula I or a pharmaceutically acceptable salt thereof.

DETAILED DESCRIPTION AND PREFERRED EMBODIMENTS

All temperatures stated herein are in degrees Celsius (°C.). All units of measurement employed herein are in weight units except for liquids which are in volume units.

As used herein, the term "$C_1$-$C_6$ alkyl" represents a straight or branched alkyl chain having from one to six carbon atoms. Typical $C_1$-$C_6$ alkyl groups include methyl, ethyl, propyl, isopropyl, butyl, isobutyl, sec-butyl, t-butyl, pentyl, neo-pentyl, hexyl and the like. The term "$C_1$-$C_6$ alkyl" includes within its definition the term "$C_1$-$C_4$ alkyl".

"Halo" represents chloro, fluoro, bromo or iodo.

"$C_1$-$C_6$ alkoxy" represents a straight or branched alkyl chain having from one to six carbon atoms attached to an oxygen atom. Typical $C_1$-$C_6$ alkoxy groups include methoxy, ethoxy, propoxy, isopropoxy, butoxy, t-butoxy, pentoxy and the like. The term "$C_1$-$C_6$ alkoxy" includes within its definition the term "$C_1$-$C_4$ alkoxy".

"$C_2$-$C_6$ alkanoyl" represents a straight or branched alkyl chain having from one to five carbon atoms attached to a carbonyl moiety. Typical $C_2$-$C_6$ alkanoyl groups include ethanoyl, propanoyl, isopropanoyl, butanoyl, t-butanoyl, pentanoyl, hexanoyl, 3-methylpentanoyl and the like.

"$C_1$-$C_4$ alkoxycarbonyl" represents a straight or branched alkoxy chain having from one to four carbon atoms attached to a carbonyl moiety. Typical $C_1$-$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "carboxy-($C_1$-$C_6$ alkoxy)-" as used herein refers to a moiety of the structure

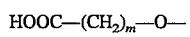

where m is 1–6, inclusive.

The term "carboxy-($C_1$-$C_6$ alkyl)-" as used herein refers to a moiety of the structure

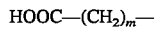

where m is 1 to 6, inclusive.

The term "hydroxy-protecting groups" as used herein refers to substituents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2 -dichloro-1,1-difluoroethyl, tetrahydropyranyl, phenacyl, cyclopropylmethyl, allyl, $C_1$-$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of such groups may be found in T. W. Greene and P. G. M. Wuts, "Protective Groups in Organic Synthesis" (1991) at Chapter 3.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and preferably may be, for example, succinimidoxy, phthalimidoxy, benzotriazolyloxy or —O—CO—($C_4$-$C_7$ alkyl).

The compounds used in the method of the present invention may have one or more asymmetric centers. As a consequence of these chiral centers, the compounds of the present invention occur as mixture of enantiomers, racemates, racemic mixtures and as individual enantiomers. All asymmetric forms, individual isomers and combinations thereof, are within the scope of the present invention.

As mentioned supra, the invention encompasses methods employing the pharmaceutically acceptable salts of the compounds defined by Formula I. A compound employed in this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

The preferred methods of this invention employ those compounds in which:

$R^1$ is hydrogen, acetyl, propanoyl, methoxy, ethoxy, methoxycarbonyl, ethoxycarbonyl, methyl, ethyl, n-propyl, isopropyl, phenyl, monosubstituted phenyl, disubstituted phenyl, and trisubstituted phenyl;

$R^2$ is hydroxy, methoxy, ethoxy, hydrogen, methyl, ethyl, n-propyl, and isopropyl;

$R^3$ is hydrogen, methyl, ethyl, n-propyl, isopropyl, and n-butyl;

n is 1 to 4;

B is —O—, —CH$_2$—, or —C($R^5R^6$)—, where $R^5$ and $R^6$ are independently methyl, ethyl, or hydrogen; and $R^4$ is phenyl, xanthenyl, tetrazolyl, or 3,4-dihydrobenzopyranyl, said moieties being mono- or di-substituted with methyl, ethyl, propyl, isopropyl, butyl, methoxy, ethoxy, propoxy, butoxy, pentoxy, oxo, carboxy, The compounds of this invention may be prepared according to standard methods known in the art. Many of the compounds employed in the methods of the present invention can be prepared by the methodology described in U.S. Pat. No. 4,945,099, issued Jul. 31, 1990, which is herein incorporated by reference. For example, the tetrazole compounds of Formula I may be prepared from the corresponding intermediate of Formula II

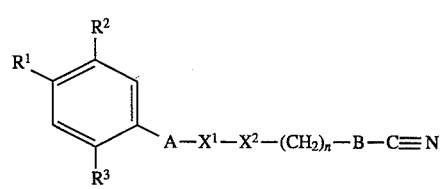

by any of a variety of standard methods. Generally, the nitrile is reacted with an azide reagent in a non-reactive solvent. Preferred conditions include the use of lithium or ammonium azide in dimethylformamide, sodium azide in diglyme and N,N-dimethylethanolamine hydrochloride, or tri-n-butyltin azide in a non-reactive solvent such as dimethoxyethane or tetrahydrofuran. Under the latter conditions, the reaction is generally heated at or near the reflux temperature of the reaction mixture. The transformation is generally complete under these conditions in 2–3 days. Other operable reaction conditions include the reaction of the nitrile of Formula II with an alkali metal azide such as sodium azide, ammonium chloride, and (optionally) lithium chloride in a non-reactive high-boiling solvent such as N,N-dimethylformamide, preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and N,N-dimethylformamide.

Similarly, the acids of this invention are prepared from the corresponding esters or nitriles. Hydrolysis of such esters or nitriles may be accomplished by any of a variety of acidic or basic conditions, preferably under aqueous conditions. Preferred methods involve the use of lithium hydroxide in a solvent mixture of acetone and water, sodium hydroxide in dioxane, or potassium hydroxide or potassium carbonate in a mixture of methanol and water. Under the former conditions, hydrolysis is generally complete in about 12–18 hours at temperatures from about 20°–30° C. whereas the latter reaction is usually complete in one hour at 20°–30° C.

It is generally preferred, in compounds containing both a nitrile and an ester functionality, that the nitrile group be transformed into a tetrazole before hydrolysis of the ester.

Compounds of Formula I as well as intermediates in the preparation of the compounds of Formula I can be prepared by a number of synthetic routes as will be appreciated by skilled artisans depending upon the particular compound desired. For those compounds wherein A is —O—, the following scheme is generally applicable:

Scheme I

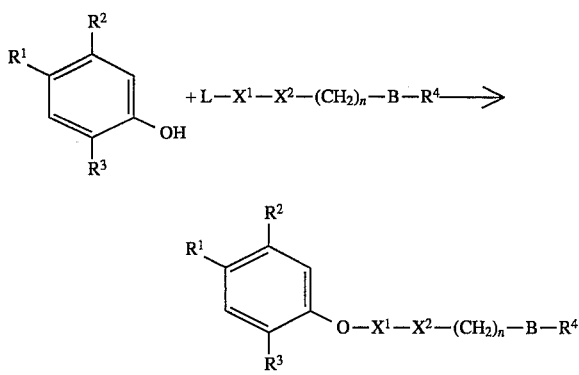

where L is a good leaving group such as halo, especially chloro, bromo or iodo, and $R^2$ is hydroxy or, preferably, a protected hydroxy group, such as benzyloxy.

The reaction of Scheme I is usually performed employing equimolar amounts of the two reactants although ratios other than equimolar amounts are completely operative. The reaction is best carried out in a nonreactive solvent such as a ketone, especially acetone or methyl ethyl ketone, or dimethylformamide, and in the presence of a base, preferably an alkali metal hydride or carbonate, preferably potassium carbonate. Especially when L is chloro, a catalyst such as potassium or sodium iodide may be added to increase the reaction rate. The reaction may be carried out at temperatures of about ambient temperature up to the boiling point of the reaction mixture, the former being preferred.

In the preferred case where the hydroxy group has been protected, the protecting group is removed following the coupling procedure described above. As will be appreciated by skilled artisans in the field, the means for deprotecting the hydroxy group will depend upon the choice of protecting group employed. In the preferred situation where a benzyl group is used, the benzyl group is removed by catalytic hydrogenation, for example, in the presence of 10% palladium on activated carbon in ethyl acetate, to provide the desired phenol. Usually this coupling reaction is perfomed before the final deprotecting of the $R^4$ moiety; however, as will be appreciated, it is possible this sequence can be reversed depending on the functional groups involved. Thus, coupling as noted above may, under certain circumstances well appreciated in the art, first involve transformation of the nitrile into 5-tetrazolyl followed by deprotection of the phenol.

A similar reaction protocol is found in Scheme II:

Scheme II

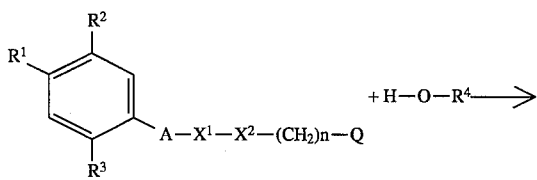

-continued
Scheme II

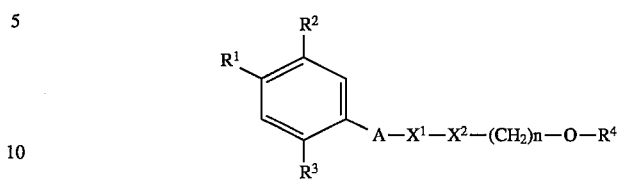

where Q is bromo, chloro, iodo, mesyl, tosyl, or a similar leaving group. Aspects of this reaction scheme and all the variations thereof are generally the same as discussed above regarding Scheme I.

Other interconversions of compounds are readily apparent to skilled artisans. For example, when $R^4$ is halo, compounds treated with cyanide, such as potassium or sodium cyanide, in a non-reactive solvent such as dimethylformamide, are transformed into cognates wherein $R^4$ is —CN. The use of a catalytic amount of iodide is employed to speed the reaction. Such nitriles can then be converted into tetrazoles as described above, or hydrolyzed in the presence of a base, such as sodium or potassium hydroxide, in alcoholic water to provide the corresponding carboxylic acids. An alternate process for converting halides into nitriles involves the displacement by carbon anions in sodium amide and liquid ammonia as described in U.S. Pat. No. 4,945,099.

Other transformations are also well known to those skilled in the art of organic chemistry. Carboxylic acids can be esterified by standard means, or converted to acid halides which are then reacted with amines to provide the corresponding amides. Similarly, esters, amides, and nitriles may be hydrolyzed to the carboxylic acid. Nitriles can also be hydrolyzed to the primary amide by treatment with aqueous base.

The terms and abbreviations used in the instant examples have their normal meanings unless otherwise designated. For example "N" refers to normal or normality; "mmole" or "mmoles" refers to millimole or millimoles; "g" refers to gram or grams; "ml" means milliliter or milliliters; "M" refers to molar or molarity; "eqv" refers to molar equivalents; "FDMS" refers to field desorption mass spectrometry; "MS" refers to mass spectrometry, and "NMR" refers to nuclear magnetic resonance.

The following examples further illustrate the preparation of the compounds of Formula I. These examples are illustrative only and are not intended to limit the scope of the invention in any way. In those compounds in which the terms "NMR" or "MS", or both, follow the synthesis protocol, these terms indicate that the identity of the compounds was confirmed using nuclear magnetic resonance (NMR), mass spectrometry (MS) or both.

EXAMPLE 1

N,N-Dimethyl-3-(2-(3-(2-ethyl-4-(4-fluorophenyl)-5-hydroxyphenoxy)propoxy)phenyl)propionamide

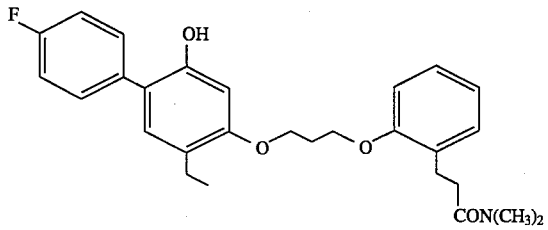

A solution of 1.5 g of 3-(2-ethyl-4-bromo-5-benzyloxyphenoxy)propyl chloride and 0.5 g of tetrakis-(triphenylphosphine)palladium(0) in 70 ml of benzene was stirred with 15 ml of 2.0M sodium carbonate. A solution of 1.1 g of 4-fluorophenyl boronic acid in 15 ml of ethanol was added. The mixture was heated at reflux for 16 hours. The mixture was cooled and diluted with ethyl acetate. The organic phase was washed with saturated ammonium chloride, washed with saturated sodium chloride, dried over sodium sulfate, and evaporated in vacuo. The residue was chromatographed on silica gel eluting with hexane/ethyl ether to provide 1.44 g (93%) of the desired title intermediate. NMR.

A mixture of 11 g of resorcinol, 8.8 g of 3-(2-ethyl-4-(4-fluorophenyl)-5-benzyloxyphenoxy)propyl chloride, and 13.8 g of potassium iodide in 150 ml of dimethylformamide was heated in an oil bath at 90° C. for 24 hours. The mixture was cooled, diluted with water, and extracted with ethyl acetate. The organic phase was washed with water, washed with saturated sodium chloride, dried over sodium sulfate, and evaporated in vacuo. The residue was chromatographed on silica gel eluting with hexane/ethyl ether providing the title intermediate in 34% yield, NMR.

A solution of 375 mg of ethyl 3-(2-(3-(2-ethyl-4-(4-fluorophenyl)-5-benzyloxyphenoxy)propoxy)phenyl)propionate in 25 ml of ethanol was mixed with 5 ml of 5.0N sodium hydroxide and stirred 16 hours. The mixture was diluted with 1.0N hydrochloric acid and extracted with 3:1 dichloromethane/isopropanol. The organic phase was washed with saturated sodium chloride, dried over sodium sulfate, and evaporated in vacuo providing the desired 3-(2-(3-(2-ethyl-4-(4-fluorophenyl)-5-hydroxyphenoxy)propoxy)phenyl)propionic acid in 93% yield. NMR.

A solution of 3-(2-(3-(2-ethyl-4-(4-fluorophenyl)-5-hydroxyphenoxy)propoxy)phenyl)propionic acid and several equivalents of thionyl chloride in dichloromethane was kept at room temperature for 3 hours, and then poured into a stirred solution of 40% dimethylamine in water. The organic layer was washed with aqueous hydrochloric acid, washed with saturated sodium chloride, dried over sodium sulfate, and evaporated in vacuo. The residue was chromatographed on silica gel eluting with ethyl acetate to provide the desired title product. NMR, MS.

EXAMPLE 2

N-Methanesulfonyl-3-(2-(3-(2-ethyl-4-(4-fluorophenyl)-5-hydroxyphenoxy)propoxy)phenyl)propionamide

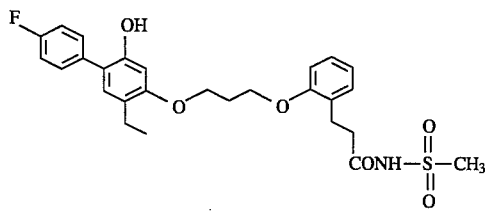

A solution of 3-(2-(3-(2-ethyl-4-(4-fluorophenyl)-5-hydroxyphenoxy)propoxy)phenyl)propionic acid and several equivalents of thionyl chloride in dichloromethane was maintained at room temperature for 3 hours to produce the acid chloride. To this acid chloride in tetrahydrofuran was added a suspension of 10 equivalents of N-lithiomethanesulfonamide in tetrahydrofuran at −5° C. The mixture was allowed to warm to room temperature, diluted with aqueous hydrochloric acid, and extracted with ethyl acetate. The organic solution was dried and evaporated in vacuo. The residue was chromatographed on silica gel eluting with dichloromethane/methanol to provide the desired title intermediate in 37% yield. NMR.

EXAMPLE 3

N-Phenylsulfonyl-3-(2-(3-(2-ethyl-4-(4-fluorophenyl)-5-hydroxyphenoxy)propoxy)phenyl)propionamide

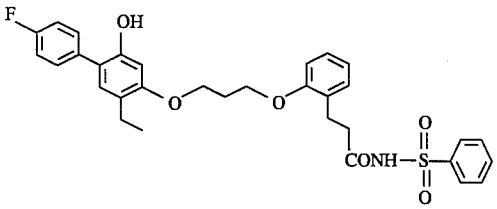

The title product was prepared by the procedure of Example 2 using N-lithiobenzenesulfonamide. The product was isolated by preparative $C_{18}$ reverse phase HPLC. NMR.

EXAMPLE 4

Preparation of
2-phenyl-4-ethyl-5-[[6-(2H-tetrazol-5-yl)-6-methylheptyl]oxy]phenol

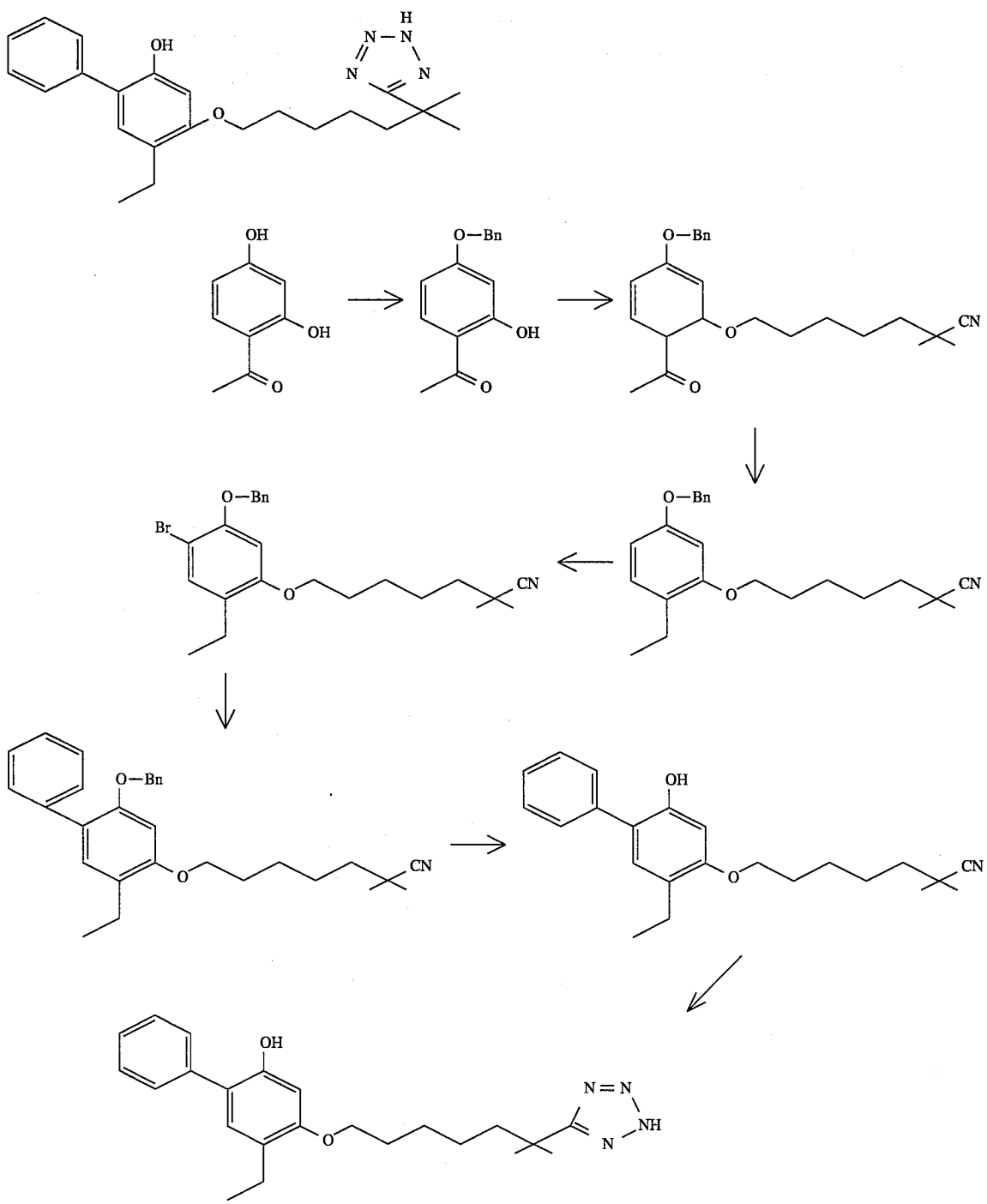

Synthesis of
1-Benzyloxy-2-phenyl-4-ethyl-5-(6-methyl-6-cyanoheptyloxy)benzene

A. Preparation of 4-benzyloxy-2-hydroxyacetophenone.

In a dry round-bottom flask under nitrogen, 2,4-dihydroxyacetophenone (15.2 g, 100 mmoles) was dissolved in methyl ethyl ketone (400 ml) and dimethylsulfoxide (100 ml). To this solution were added benzyl bromide (17.0 g, 100 mmoles) and potassium carbonate (27.6 g, 200 mmoles). The reaction was heated to reflux and stirred for 15 hours. The methyl ethyl ketone was removed in vacuo, and the dimethylsulfoxide solution was diluted with ethyl acetate and washed several times with brine. The organic material was collected, dried (magnesium sulfate), filtered, and concentrated to provide a dark solid. The solid was recrystallized from hexane/toluene to provide the title benzyl ether as a tan solid (12.8 g, 55.7%); mp 143°–144.5° C.; NMR (CDCl$_3$) $\partial$12.77 (s, 1H), 7.70 (d, 1H, J=7 Hz), 7.3–7.5 (m, 5H), 6.54 (d, 1H, J=7 Hz), 6.53 (s, 1H), 5.11 (s, 2H), 2.58 (s, 3H). Analysis for C$_{15}$H$_{12}$O$_3$: Theory: C, 74.36; H, 5.82; Found: C, 74.52; H, 5.97.

B. Preparation of 2-(6-methyl-6-cyanoheptyloxy)-4-benzyloxyacetophenone.

To a solution of 4-benzyloxy-2-hydroxyacetophenone (9.65 g, 42 mmoles) in dimethylformamide (150 ml) were added the appropriate alkyl chloride (6.86 g, 40 mmoles), potassium carbonate (10.6 g, 77 mmoles), and potassium iodide (1.6 g, 9.6 mmoles). The stirred reaction was heated to 90° C. for 24 hours. The solids were removed by filtration, and the dimethylformamide was removed in vacuo. The residue was purified by Prep-500 HPLC, using a gradient of 5% ethyl acetate in hexane to 20% over 30 minutes as a mobile phase to yield the title ether as a clear oil (12.1 g, 79.8%); NMR (CDCl$_3$) ∂7.85 (d, 1H, J=7.4 Hz), 7.3–7.5 (m, 5H), 6.60 (dd, 1H, J=7.4, 1.8 Hz), 6.53 (d, 1H, J=1.8 Hz), 5.12 (s, 2H), 4.04 (t, 2H, J=5.3 Hz), 2.61 (s, 3H), 1.85–1.95 (m, 2H), 1.5–1.6 (m, 6H), 1.37 (s, 6H); IR (CHCl$_3$) 2943, 2238, 1601 cm$^{-1}$; MS (m/e) 379.

C. Preparation of 4-benzyloxy-2-(6-methyl-6-cyanoheptyloxy)ethylbenzene.

To a solution of 2-(6-methyl-6-cyanoheptyloxy)-4-benzyloxyacetophenone (12.1 g, 31.6 mmoles) in carbon tetrachloride (30 ml) were added trifluoroacetic acid (44.4 g, 390 mmoles) and triethylsilane (21.8 g, 188 mmoles). The reaction was stirred at room temperature for 1.5 hours, then was worked-up by diluting with ethyl acetate and washing with aqueous sodium carbonate. The organic material was collected, dried (magnesium sulfate), filtered, and concentrated in vacuo. The residue was purified by Prep-500 HPLC using a 3% ethyl acetate in hexane to 5% grade over 15 minutes, then holding at 5%. Concentration of the appropriate fractions provided the desired title product (10.6 g, 91.5%) as a clear liquid. NMR (CDCl$_3$) ∂7.35–7.5 (m, 5H), 7.06 (d, 1H, J=6.5 Hz), 6.53 (s, 1H), 6.52 (dd, 1H, J=6.5, 2 Hz), 5.06 (s, 2H), 3.96 (t, 2H, J=5.3 Hz), 2.60 (q, 2H, J=6.3 Hz), 1.8–1.85 (m, 2H), 1.5–1.6 (m, 6H), 1.37 (s, 6H), 1.20 (t, 3H, J=6.3 Hz).

D. Preparation of 1-bromo-2-benzyloxy-4-(6-methyl-6-cyanoheptyloxy)-5-ethylbenzene.

To a stirred solution of 4-benzyloxy-2-(6-methyl-6-cyanoheptyloxy)ethylbenzene (10.6 g, 28.9 mmoles) in carbon tetrachloride (125 ml) was added N-bromosuccinimide (6.0 g, 33.3 mmoles). Stirring was continued for 6 hours at room temperature. The mixture was then diluted with methylene chloride and washed with water. The organic material was collected, dried (magnesium sulfate), filtered, and concentrated in vacuo. The residue was recrystallized from hexane/ethyl acetate to provide the title aryl bromide (12.6 g, 97.8%) as a pale yellow solid. NMR (CDCl$_3$) ∂7.35–7.5 (m, 5H), 7.22 (s, 1H), 6.50 (s, 1H), 5.17 (s, 2H), 3.90 (t, 2H, J=5.3 Hz), 2.58 (q, 2H, J=6.3 Hz), 1.75–1.85 (m, 2H), 1.50–1.65 (m, 6H), 1.37 (s, 6H), 1.18 (t, 3H, J=6.3 Hz); IR (CHCl$_3$) 3020, 2981, 2946, 2238, 1662, 1600 cm$^{-1}$; MS (m/e) 444, 445, 446.

E. Representative procedures for the biaryl coupling reaction.

Method A

In a round-bottom flask, the appropriate aryl bromide (1 equivalent) was dissolved in benzene. To this solution were added Pd(PPh$_3$)$_4$ (10 mole %) and a 2.0M aqueous solution of sodium carbonate (10 eq.). In a separate flask, the aryl boronic acid (2 eq.) was dissolved in ethanol. To the aryl boronic acid solution was added the the aryl bromide solution, and the mixture was heated to reflux and stirred for 16 hours. The mixture was diluted with ethyl acetate and washed with saturated aqueous ammonium chloride. The organic material was collected, dried (magnesium sulfate), filtered, and concentrated. The residue was purified by flash chromatography (6% ethyl acetate in hexane) to provide the desired biaryl.

Method B

A solution of the appropriate aryl bromide in tetrahydrofuran was cooled to −78° C. To this solution was added tert-butyl lithium (2 eq). The reaction was stirred at −78° C. for 30 minutes, then a tetrahydrofuran solution of zinc chloride (1 eq) was added. The mixture was warmed to room temperature and stirred for 15 minutes. In a separate flask, a solution was prepared containing the appropriate aryl halide (1 eq) and Pd(PPh$_3$)$_4$ (10 mole %) in tetrahydrofuran. This solution was added to the aryl zinc solution, and the mixture was stirred at room temperature for 2–18 hours. The reaction was diluted with ethyl acetate and washed with aqueous ammonium chloride. The organic material was dried (magnesium sulfate), filtered, and concentrated. The residue was purified by flash chromatography (6% ethyl acetate in hexane) to provide the desired biaryl.

F. Preparation of 1-benzyloxy-2-phenyl-4-ethyl-5-(6-methyl-6-cyanoheptyloxy)benzene.

This compound was prepared in 75% yield by Method A. NMR (CDCl$_3$) ∂7.60 (d, 2H, J=6.5 Hz), 7.3–7.5 (m, 8H), 7.18 (s, 1H), 6.59 (s, 1H), 5.04 (s, 2H), 3.95 (t, 2H, J=5.3 Hz), 2.63 (q, 2H, J=6.3 Hz), 1.8–1.9 (m, 2H), 1.5–1.65 (m, 6H), 1.38 (s, 6H), 1.25 (t, 3H, J=6.3 Hz); IR (CHCl$_3$) 3013, 2977, 2943, 2238, 1611, 1488 cm$^{-1}$; MS (m/e) 439. Analysis for C$_{30}$H$_{35}$NO$_2$: Calc: C, 81.59; H, 7.99; N, 3.17; Found: C, 81.34; H, 8.18; N, 3.05.

To a solution of the nitrile (1 eq.) in diglyme were added N,N-dimethylethanolamine hydrochloride (2 eq.) and sodium azide (4 eq.). The suspension was heated to 130° C. and stirred for up to 72 hours. The mixture was diluted with methylene chloride and acidified with dilute hydrochloride acid. The organic material was collected, dried (magnesium sulfate), filtered and concentrated in vacuo. The resulting material was dissolved in ethanol, and to this solution was added aqueous sodium hydroxide (4 eq.). This reaction was stirred at room temperature for 30 minutes, then the solvents were removed in vacuo. An HP-20 reverse phase MPLC system was used to purify the residue, first using water as the mobile phase, then using 40% water in methanol. The desired fractions were combined and concentrated in vacuo. The residue was then lyophilized to produce the tetrazole as its sodium salt.

2-Phenyl-4-ethyl-5-[6-(2H-tetrazol-5-yl)-6-methylheptyloxy]phenol sodium salt, 34.3% yield. NMR (DMSO-d6) ∂7.55 (d, 2H, J=6.5 Hz), 7.35 (t, 2H, J=6.5 Hz), 7.20 (t, 1H, J=6.5 Hz), 6.98 (s, 1H), 6.60 (s, 1H), 3.82 (t, 2H, J=5.3 Hz), 2.65 (q, 2H, J=6.3 Hz), 1.55–1.70 (m, 6H), 1.25–1.35 (m, 8H), 1.10 (t, 3H, J=6.3 Hz); IR (KBr) 3192, 2970, 2937, 1617, 1488, 1453, 1214 cm$^{-1}$; MS (m/e) 439. Analysis for C$_{23}$H$_{29}$N$_4$NaO$_2$·2H$_2$O: Calc: C, 59.87; H, 7.16; N, 12.25; Found: C, 60.28; H, 7.45; N, 12.07.

EXAMPLE 5

2-[3-[3-[(5-Ethyl-2-hydroxy[1,1'-biphenyl]-4-yl)oxy]propoxy]-2-propylphenoxy]propanoic acid

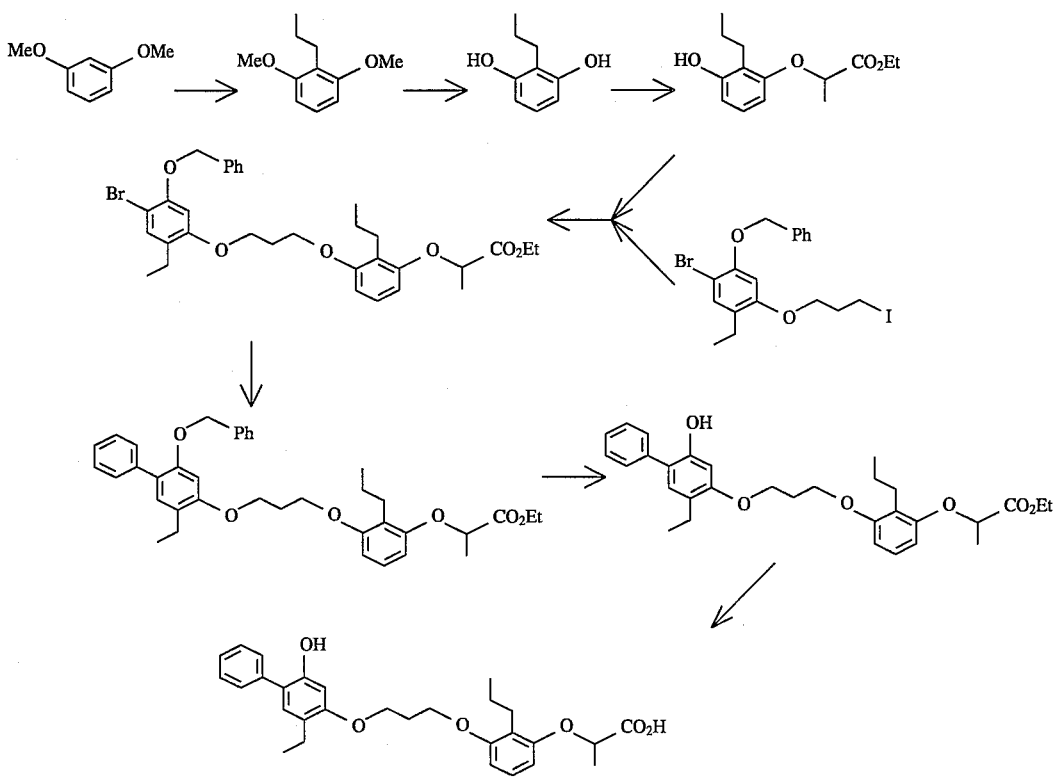

A. Preparation of 2-propyl-1,3-dimethoxybenzene.

1,3-Dimethoxybenzene (20 g, 145 mmoles) in 200 ml of dry tetrahydrofuran was cooled to −10° C. To this solution at −10° C. was added n-butyllithium (100 ml of a 1.6M solution in hexane, 160 mmoles) over 20 minutes. The reaction was then stirred for 2.5 hours at 0° C. At 0° C., propyl iodide (24.65 g, 145 mmoles) was added slowly over 15 minutes. When the addition was complete, the reaction was allowed to warm to room temperature and stirred overnight. After stirring overnight, the reaction was refluxed for 1.5 hours, then cooled to room temperature and quenched with ice. The tetrahydrofuran was removed under vacuum, and the resulting aqueous layer was extracted several times with diethyl ether. The organic extract was dried over magnesium sulfate and filtered to give a clear oil after solvent removal (26.11 g). The oil was purified by vacuum distillation to provide the title intermediate (24.0 g, 92%).

Bp 80°–82° C. at 10 mm Hg.

NMR (CDCl$_3$) ∂7.16 (t,1, J=8.30 Hz), 6.58 (d, 2, J=8.30 Hz), 3.85 (s, 6), 2.67 (t, 2, J=7.57 Hz), 1.56 (m, 2), 0.99 (t, 3, J=7.35 Hz).

B. Preparation of 2-propyl-1,3-dihydroxybenzene.

A mixture of solid 1,3-dimethoxy-2-propylbenzene (33.70 g, 190 mmoles) and solid pyridine hydrochloride (150 g, 1.30 mole) was warmed to 180° C. After 7.5 hours the reaction was cooled to 110° C. and 50 ml of water was added slowly. After the reaction cooled to room temperature, it was diluted with 100 ml of water and extracted several times with ethyl acetate. The ethyl acetate extract was washed once with 2N hydrochloric acid and then dried over magnesium sulfate. Filtration and solvent removal gave 38.5 g of an orange solid. The title product was purified by recrystallization from dichloromethane providing 11.86 g (41%) of yellow crystals.

NMR (CDCl$_3$) ∂6.94 (t, 1, J=8.10 Hz), 6.40 (d, 2, J=8.10 Hz), 4.84 (s, 2), 2.63 (t, 2, J=7.57 Hz), 1.62 (m, 2), 1.01 (t, 3, J=7.33 Hz).

C. Preparation of ethyl 2-(2-propyl-3 -hydroxyphenoxy)-propanoate.

Sodium hydride (1.08 g of a 60% oil dispersion, 27 mmoles) under an argon atmosphere was washed with 15 ml of dry hexane. The hexane supernatant was removed via syringe. Dry tetrahydrofuran (60 ml) was added to the sodium hydride and, with stirring at room temperature, the 2-propyl-1,3-dihydroxybenzene (4.08 g, 27 mmoles) was added as a 40 ml tetrahydrofuran solution. After stirring at room temperature for 25 minutes, the ethyl 2-bromopropionate (4.64 g, 26 mmoles) was added rapidly. After stirring at room temperature for 17 hours, the reaction was quenched with a saturated aqueous ammonium chloride solution and the tetrahydrofuran was removed under vacuum. The resulting aqueous mixture was extracted several times with ethyl acetate. The organic extract was dried over magnesium sulfate. Filtration and solvent removal gave an orange oil. This oil was purified by flash chromatography on silica gel eluting with 20% ethyl acetate/hexane. The desired title ester was obtained as a white solid (2.43 g, 36%).

TLC: Rf=0.47 (30% ethyl acetate/hexane) NMR (CDCl$_3$) ∂6.93 (dd, 1, J=8.00 Hz), 6.45 (d, 1, J=8.00 Hz), 6.30 (d, 1, J=8.00 Hz), 5.77 (s, 1), 4.76 (q, 1, J=6.76 Hz), 4.23 (q, 2, J=7.02 Hz), 2.69 (m, 2), 1.63 (d, 3, J=6.70 Hz), 1.60 (m, 2), 1.28 (t, 3, J=7.50 Hz), 0.99 (t, 3, J=7.50 Hz); IR (KBr) 3435, 2955, 2872, 1733, 1600, 1500, 1465 cm$^{-1}$; Mass Spec. (FD) (m/z) 253 (M$^+$+1). Analysis for C$_{14}$H$_{20}$O$_4$: Calc: C, 66.65; H, 7.99; Found: C, 66.41; H, 8.04.

D. Preparation of ethyl 2-[3-[3-[(2-benzyloxy-1-bromo-5-ethyl-4-yl)oxy]propoxy]-2 -propylphenoxy]propanoate.

Ethyl 2-(2-propyl-3-hydroxyphenoxy)propanoate was dissolved in methyl ethyl ketone (60 ml), and solid sodium iodide (20 g, 133 mmoles) was added. The reaction mixture was refluxed under an argon atmosphere for 18 hours. The reaction was cooled to room temperature, quenched with water, then extracted three times with diethyl ether. The organic extracts were combined, dried over magnesium sulfate, and filtered to give 6.27 g of a yellow oil.

A solution of ethyl 3,4-dihydro-7-hydroxy-8-propyl-2H-1-benzopyran-2-carboxylate (2.1 g, 8.1 mmoles) in dimethylformamide (5 ml) was added to a suspension of sodium hydride (324 mg, 8.1 moles, 60% oil dispersion) in 10 ml of dry dimethylformamide under a nitrogen atmosphere. After stirring the reaction mixture for 30 minutes, a mixture of the alkyl iodide (3.8 g, 8.1 mmoles) prepared above and 18-Crown-6 (110 mg, 0.4 mmole) was added. The reaction was stirred for 1.5 hours at room temperature. The reaction was quenched with water and then extracted several times with ethyl acetate. The organic material was dried over magnesium sulfate, filtered and concentrated under vacuum. The resulting product was purified by flash chromatography on silica gel eluting with 6% ethyl acetate/hexane to give the title intermediate as a clear oil (2.90 g, 68% yield).

TLC: Rf=0.47 (30% ethyl acetate/hexane) NMR (CDCl$_3$) ∂7.56–7.37 (m, 6), 7.12 (t, 1, J=8.20 Hz), 6.62 (d, 1, J=8.35 Hz), 6.59 (s, 1), 6.45 (d, 1, J=8.31 Hz), 5.16 (s, 2), 4.80 (q, 1, J=6.90 Hz), 4.26 (q, 2, J=7.20 Hz), 4.18 (dd, 4, J=5.91, 12.02 Hz), 2.80 (m, 2), 2.62 (q, 2, J=7.47 Hz), 2.31 (m, 2), 1.69 (d, 3, J=6.70 Hz), 1.65 (m, 2), 1.30 (t, 3, J=7.20 Hz), 1.22 (t, 3, J=7.54 Hz), 1.03 (t, 3, J=7.35 Hz); IR (CHCl$_3$) 3015, 2967, 2930, 2780, 1752, 1595, 1500, 1464 cm$^{-1}$; Mass Spec. (FAB) (m/z) 599 (M$^+$). Analysis for C$_{32}$H$_{39}$BrO$_6$: Calc: C, 64.11; H, 6.56; Br, 13.33; Found: C, 64.01; H, 6.56; Br, 13.06.

E. Preparation of ethyl 2-[3-[3-[(2-benzyloxy-5-ethyl[1,1'-biphenyl]-4-yl)oxy]propoxy]-2-propylphenoxy]propanoate.

Ethyl 2-[3-[3-[(2-benzyloxy-1-bromo-5-ethyl-4-yl)oxy]propoxy]-2-propylphenoxy]propanoate (1.3 g, 2.24 mmoles) was stirred in 40 ml of benzene under an argon atmosphere. To this solution was added tetrakis(triphenylphosphine)palladium(0) (0.40 g, 0.35 mmole) and sodium bicarbonate (10 ml of a 2M aqueous solution). An ethanol solution (10 ml) of phenylboronic acid (1.3 g, 10.7 mmoles) was added to the above reaction mixture, and then the reaction mixture was refluxed for 21 hours. The reaction was cooled to room temperature, quenched with a saturated aqueous ammonium chloride solution, diluted with water and then extracted with ethyl acetate. The organic layer was dried over magnesium sulfate and filtered. The filtrate was concentrated under vacuum providing 1.3 g of a brown solid. The solid was dissolved in 20% ethyl acetate/hexane and filtered through 35 g of Merck 60 silica gel eluting with 500 ml of 20% ethyl acetate/hexane. The resulting 1.0 g of yellow oil was purified by flash chromatography on silica gel eluting with 18% ethyl acetate/hexane. The desired title ester was obtained in 47% yield as a clear oil.

TLC: Rf=0.48 (30% ethyl acetate/hexane) NMR (CDCl$_3$) ∂7.10 (d, 2, J=8.06 Hz), 7.44 (m, 8), 7.27 (s, 1), 7.15 (t, 1, J=8.14 Hz), 6.72 (s, 1), 6.66 (d, 1, J=8.27 Hz), 6.48 (d, 1, J=8.27 Hz), 5.11 (s, 2), 4.83 (q, 1, J=6.71 Hz), 4.28 (m, 6), 2.78 (m, 4), 2.38 (m, 2), 1.72 (d, 3, J=6.96 Hz), 1.69 (m, 2), 1.32 (t, 3, J=7.29 Hz), 1.31 (t, 3, J=7.30 Hz), 1.08 (t, 3, J=7.36 Hz); IR (CHCl$_3$) 3015, 2966, 2930, 2880, 1750, 1594, 1488, 1464 cm$^{-1}$; Mass Spec. (FAB) (m/z) 597 (M$^+$+1), 596 (M$^+$). Analysis for C$_{38}$H$_{44}$O$_6$: Calc: C, 76.48; H, 7.43; Found: C, 76.42; H, 7.52.

F. Preparation of ethyl 2-[3-[3-[(5-ethyl-2-hydroxy[1,1'-biphenyl]-4-yl)oxy]propoxy]-2-propylphenoxy]propanoate.

Hydrogen gas was bubbled for 15 minutes through a 10 ml ethyl acetate solution of ethyl 2-[3-[3-[(2-benzyloxy-5-ethyl[1,1'-biphenyl]-4-yl)oxy]propoxy]-2-propylphenoxy]propanoate containing 0.14 g of 10% palladium on activated carbon catalyst. A hydrogen atmosphere was maintained over the reaction mixture, and the reaction was stirred for 4 days. The reaction was filtered through a Celite® pad in a sintered glass funnel and the catalyst was washed with ethyl acetate. The solvent was removed from the filtrate providing a clear oil. The oil was purified by flash chromatography on silica gel eluting with 20% ethyl acetate/hexane. The title intermediate was obtained in 53% yield as a clear oil.

TLC: Rf=0.36 (30% ethyl acetate/hexane) NMR (CDCl$_3$) ∂7.43 (m, 5), 7.06 (d, 1, J=8.84 Hz), 6.56 (s, 1), 6.37 (d, 1, J=8.28 Hz), 5.20 (s, 1), 4.74 (q, 1, J=6.73 Hz), 4.20 (m, 6), 2.71 (m, 2), 2.61 (q, 2, J=7.58 Hz), 2.33 (t, 2, J=6.05 Hz), 1.61 (d, 3, J=6.94 Hz), 1.58 (m, 2), 1.25 (t, 3, J=7.30 Hz), 1.19 (t, 3, J=7.40 Hz), 0.96 (t, 3, J=7.35 Hz); IR (CHCl$_3$) 3558, 3029, 3011, 2964, 2935, 2873, 1745, 1625, 1593, 1488, 1464 cm$^{-1}$; Mass Spec. (FAB) (m/z) 507 (M$^+$+1), 506 (M$^+$). Analysis for C$_{31}$H$_{38}$O$_6$: Calc: C, 73.49; H, 7.56; Found: C, 73.70; H, 7.67.

G. Preparation of 2-[3-[3-[(5-ethyl-2-hydroxy[1,1'-biphenyl]-4-yl)oxy]propoxy]-2-propylphenoxy]propanoic acid.

A solution of ethyl 2-[3-[3-[(5-ethyl-2-hydroxy[1,1'-biphenyl]-4-yl)oxy]propoxy]-2-propylphenoxy]propanoate in 4 ml of dioxane was treated with 1.10 ml of 2N sodium hydroxide solution and stirred at room temperature. After 1.25 hours at room temperature, the dioxane was removed under vacuum and the remaining aqueous solution was diluted with water an acidified to pH 1 with 5N hydrochloric acid. The resulting suspension was extracted with ethyl acetate. The organic extract was dried over magnesium sulfate and filtered. The resulting white solid was recrystallized from toluene/hexane. The title product was crystallized from toluene/hexane and obtained as white tufts (0.582 g, 80%).

TLC: Rf=0.21 (10% methanol/methylene chloride) NMR (CDCl$_3$) ∂7.45 (m, 5), 7.09 (t, 1, J=8.16 Hz), 7.03 (s, 1), 6.60 (d, 1, J=8.28 Hz), 6.56 (s, 1), 6.42 (d, 1, J=8.29 Hz), 4.79 (q, 1, J=7.00 Hz), 4.20 (m, 4), 2.70 (m, 2), 2.62 (q, 2, J=7.49 Hz), 2.33 (t, 2, J=6.00 Hz), 1.67 (d, 3, J=6.93 Hz), 1.56 (m, 2), 1.20 (t, 3, J=7.39 Hz), 0.96 (t, 3, J=7.30 Hz); IR (KBr) 3381, 2964, 2871, 1707, 1615, 1594, 1490, 1461 cm$^{-1}$; Mass Spec. (FAB) (m/z) 479 (M$^+$+1), 478 (M$^+$). Analysis for C$_{29}$H$_{34}$O$_6$: Calc: C, 72.78; H, 7.16; Found: C, 73.39; H, 7.29.

EXAMPLE 6

8-Propyl-7-[3-[4-(4-fluorophenyl)-2-ethyl-5-hydroxyphenoxy]propoxy]-3,4-dihydro-2H-1-benzopyran-2-carboxylic acid

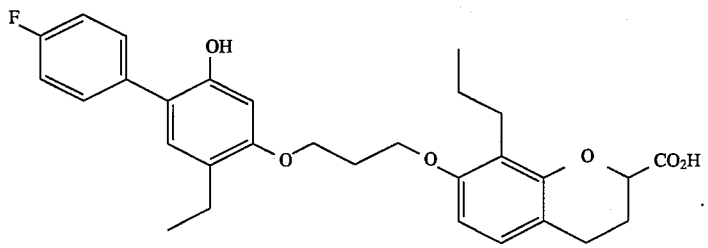

A. Preparation of ethyl 8-propyl-7-[3-[2-ethyl-4-(4-fluorophenyl)-5-benzyloxyphenoxy]propoxy]-3,4-dihydro-2H-1-benzopyran-2-carboxylate.

Tetrakis(triphenylphosphine)palladium(0) (0.659 g, 0.6 mmole) and aqueous sodium carbonate solution (20 ml of a 2M solution) were added to a 30 ml benzene solution of ethyl 7-[3-[(2-benzyloxy-1-bromo-5-ethyl-4-yl)oxy]propoxy]-3,4-dihydro-8-propyl-2H-1-benzopyran-2-carboxylate (2.163 g, 3.5 mmoles) under an argon atmosphere. The reaction was refluxed for 17 hours, then cooled to room temperature and extracted with ethyl acetate. The organic extract was dried over magnesium sulfate, filtered and the solvent removed under vacuum. The crude product was purified by Waters Prep 500 silica gel chromatography eluting with a gradient of 5% to 20% ethyl acetate/hexane over 50 minutes. The desired title biphenyl was obtained as a clear oil (1.722 g, 78%).

NMR (CDCl$_3$) ∂7.51 (m, 2), 7.32 (m, 5), 7.09 (m, 3), 6.83 (d, 1, J=8.32 Hz), 6.62 (s, 1), 6.49 (d, 1, J=8.50 Hz), 5.02 (s, 2), 4.75 (dd, 1, J=4.10, 6.50 Hz), 4.22 (m, 6), 2.69 (m, 6), 2.25 (m, 4), 1.59 (m, 2), 1.30 (t, 3, J=7.10 Hz), 1.21 (t, 3, J=7.42 Hz), 0.96 (t, 3, J=7.33 Hz); IR (CHCl$_3$) 3019, 2968, 1745, 1611, 1495 cm$^{-1}$; Mass Spec. (FAB) (m/z) 627 (M$^+$+1), 626 (M$^+$), 536. Analysis for C$_{39}$H$_{43}$O$_6$: Calc: C, 74.74; H, 6.91; F, 3.03; Found: C, 74.98; H, 7.05; F, 3.39.

B. Preparation of ethyl 8-propyl-7-[3-[4-(4-fluorophenyl)-2-ethyl-5-hydroxyphenoxy]propoxy]-3,4-dihydro-2H-1-benzopyran-2-carboxylate.

Hydrogen gas was bubbled for 10 minutes through a solution of ethyl 8-propyl-7-[3-[2-ethyl-4-(4-fluorophenyl)-5-benzyloxy-phenoxy]propoxy]-3,4-dihydro-2H-1-benzopyran-2-carboxylate (1.610 g, 2.57 mmoles) in 30 ml of ethyl acetate containing 1.0 g of 10% palladium on activated carbon catalyst. The reaction was stirred at room temperature under an atmosphere of hydrogen for 2 hours. The reaction mixture was filtered through a Celite® pad in a sintered glass funnel and the catalyst was washed with ethyl acetate. The solvent was removed from the filtrate providing 1.242 g of a clear oil. The oil was purified by flash chromatography on silica gel eluting with 20% ethyl acetate/hexane. The desired title phenol was obtained in 74% yield (1.020 g) as a white solid.

TLC: Rf=0.35 (30% ethyl acetate/hexane) NMR (CDCl$_3$) ∂7.43 (m, 2), 7.16 (dd, 2, J=5.97, 5.97 Hz), 6.98 (s,1), 6.82 (d, 1, J=8.44 Hz), 6.53 (s, 1), 6.46 (d, 1, J=9.43 Hz), 5.07 (s, 1), 4.76 (m, 1), 4.21 (m, 6), 2.67 (m, 6), 2.26 (m, 4), 1.58 (m, 2), 1.29 (t, 3, J=6.96 Hz), 1.91 (t, 3, J=7.35 Hz), 0.96 (t, 3, J=7.27 Hz); IR (KBr) 3434, 2962, 2869, 1738, 1614, 1588, 1502 cm$^{-1}$; Mass Spec (FAB) (m/z) 537 (M$^+$+1), 536 (M$^+$). Analysis for C$_{32}$H$_{37}$O$_6$: Calc: C, 71.62; H, 6.95; Found: C, 71.63; H, 7.06.

C. Preparation of 8-propyl-7-[3-[4-(4-fluorophenyl)-2-ethyl-5-hydroxyphenoxy]propoxy]-3,4-dihydro-2H-1-benzopyran-2-carboxylic acid.

A dioxane (12 ml) solution of ethyl 8-propyl-7-[3-[4-(4-fluorophenyl)-2-ethyl-5-hydroxyphenoxy]propoxy]-3,4-dihydro-2H-1-benzopyran-2-carboxylate (0.968 g, 1.8 mmoles) was treated with sodium hydroxide (2.71 ml of a 2N solution) and stirred at room temperature. After 2.5 hours at room temperature, the dioxane was removed from the reaction mixture and the remaining material was diluted with water and acidified to pH 1.0 with 5N hydrochloric acid. The resulting white milky suspension was then stirred with ethyl acetate and subsequently extracted with ethyl acetate. The organic extract was dried over magnesium sulfate, filtered and the solvent removed to give a white solid (1.098 g). The solid was recrystallized from ethyl acetate/hexane to give the title acid as white needle-like crystals (0.568 g, 62%).

TLC: Rf=0.31 (10% methanol/methylene chloride) NMR (CDCl$_3$) ∂7.42 (m, 2), 7.15 (dd, 2, J=8.68), 6.98 (s, 1), 6.85 (d, 1, J=8.30 Hz), 6.53 (s, 1), 6.52 (d, 1, J=6.98 Hz), 4.77 (dd, 1, J=3.63, 7.43 Hz), 4.18 (m, 4), 2.70 (m, 6), 2.27 (m, 4), 1.56 (m, 2), 1.19 (t, 3, J=7.42 Hz), 0.95 (t, 3, J=7.30 Hz); IR (KBr) 3421, 2959, 2871, 1706, 1615, 1500 cm$^{-1}$; Mass Spec (FAB) (m/z) 509 (M$^+$+1), 508 (M$^+$). Analysis for C$_{30}$H$_{33}$O$_6$: Calc: C, 70.78; H, 6.54; Found: C, 70.05; H, 6.82.

EXAMPLE 7

7-Carboxy-9-oxo-3-[3-(2-ethyl-5-hydroxy-4-phenylphenoxy)propoxy]-9H-xanthene-4-propanoic acid disodium salt monohydrate

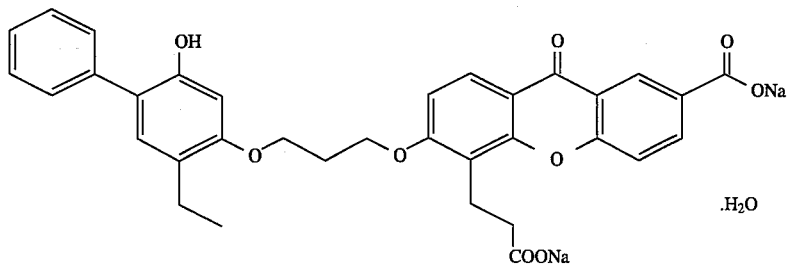

A mixture of 2-benzyloxy-1-phenyl-5-ethyl-4-(3-chloro-1-propyloxy)benzene (749 mg, 1.97 mmoles), ethyl 7-carboethoxy-3-hydroxy-9-oxo-9H-xanthene-4-propanoate (729 mg, 1.97 mmoles), potassium carbonate (1.36 g, 9.85 mmoles) and potassium iodide (33 mg, 0.20 mmoles) was refluxed for 24 hours. Dimethylsulfoxide (2 ml) was added and heating continued for 24 hours. The reaction mixture was cooled to room temperature, diluted with ethyl acetate, and washed once with water. The organic layer was dried over sodium sulfate, filtered and concentrated in vacuo to reveal a tan solid. This material was dissolved in ethyl acetate (30 ml) and the resulting solution purged with nitrogen. To this solution was added 10% palladium on carbon (120 mg) and the resulting suspension hydrogenated at 1 atmosphere of pressure. The solution was filtered and concentrated in vacuo to provide a colorless oil. This material was dissolved in a solution of 1:1 methanol/tetrahydrofuran (30 ml) and treated with 5N sodium hydroxide solution (2 ml) at room temperature for 18 hours. The resulting solution was extracted once with diethyl ether and the aqueous layer acidified with 5N hydrochloric acid solution. The resulting precipitate was collected via suction filtration. This material was converted to the di-sodium salt and purified over HP-20 resin to provide 390 mg (56%) of the desired title product as a fluffy white solid: NMR (DMSO-$d_6$) 12.65 (s, 1H, —OH), 8.65 (s, 1H), 8.28 (dd, J=8.5, 2.0 Hz, 1H), 8.01 (d, J=8.9 Hz, 1H), 7.50 (m, 3H), 7.29 (t, J=7.8 Hz, 2H), 7.17 (m, 2H), 6.93 (s, 1H), 6.89 (s, 1H), 4.26 (m, 4H), 3.12 (m, 2H), 2.47 (m, 2H), 2.23 (m, 2H), 1.10 (t, J=7.4 Hz, 3H); MS-FAB m/e 627 (24, p), 605 (40), 583 (24), 331 (24), 309 (100); IR (KBr, cm$^{-1}$) 3419 (b), 2962, 1612, 1558, 1443, 1390, 1277, 1084. Analysis for $C_{34}H_{28}O_9Na_2 \cdot H_2O$: Calc: C, 63.34; H, 4.69; Found: C, 63.36; H, 4.50.

EXAMPLE 8

2-[2-Propyl-3-[3-[2-ethyl-4-(4-fluorophenyl)-5-hydroxyphenoxy]propoxy]phenoxy]benzoic acid

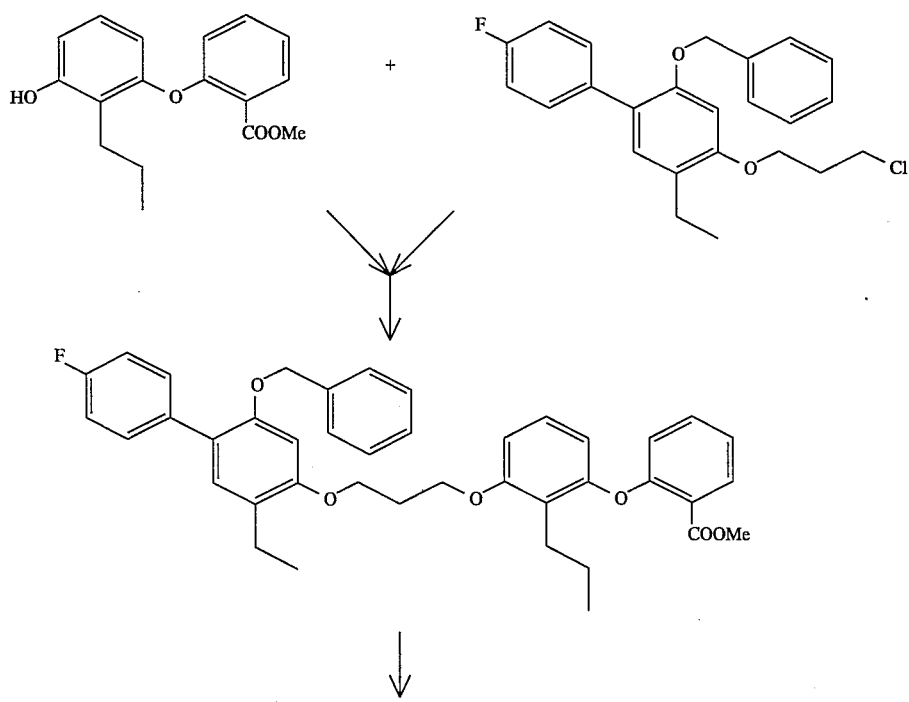

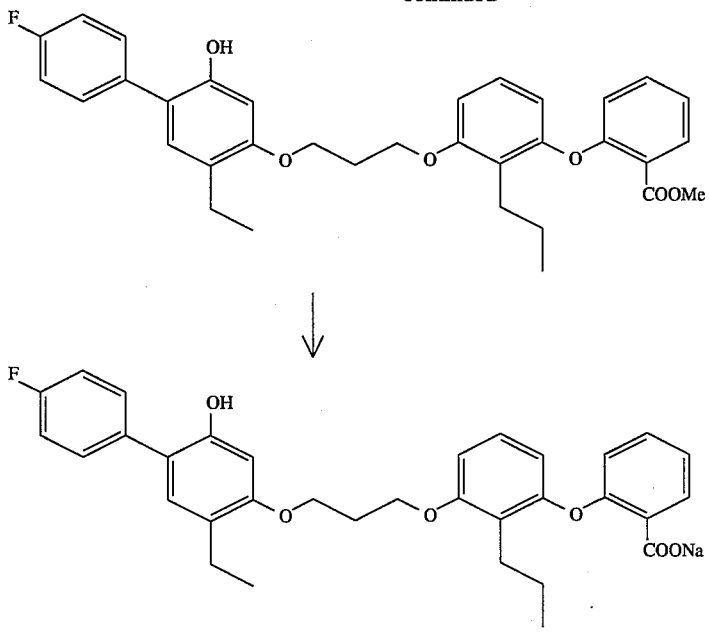

A. Preparation of 2-[2-propyl-3-[3-[2-ethyl-4-(4-fluorophenyl)-5-(phenylmethoxy)phenoxy]propoxy]phenoxy] benzoic acid methyl ester.

A mixture of 2-benzyloxy-1-(4-fluorophenyl)-5-ethyl-4-(3-chloro-1-propyloxy)benzene (20.0 g, 50.2 moles) and sodium iodide (75.3 g, 502 moles) in 2-butanone (200 ml) was refluxed for 6 hours. The mixture was diluted with ether and washed once with water. The organic layer was dried over sodium sulfate, filtered, and concentrated in vacuo to provide a colorless oil. This material was dissolved in dimethylformamide (100 ml) and treated with 2-(3-hydroxy-2-propylphenoxy)benzoic acid methyl ester (14.4 g, 50.2 mmoles) and potassium carbonate (20.8 g, 151 mmoles) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (d, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p) ; IR (CHCl$_3$, cm$^{-1}$) 2960, 1740, 1604, 1497, 1461, 1112. Analysis for C$_{41}$H$_{41}$O$_6$F: Calc: C, 75.91; H, 6.37; Found: C, 76.15; H, 6.45.

B. Preparation of 2-[2-propyl-3-[3-[2-ethyl-4-(4-fluorophenyl)-5-hydroxyphenoxy]propoxy]phenoxy]benzoic acid methyl ester.

2-[2-Propyl-3-[3-[2-ethyl-4-(4-fluorophenyl)-5-(phenylmethoxy)phenoxy]propoxy]phenoxy]benzoic acid methyl ester (33.0 g, 50.9 mmoles) was de-benzylated as described above for the preparation of Example 7 to provide 27.3 g (96%) of the title intermediate as an amber oil: NMR (CDCl$_3$) 7.90 (dd, J=7.8, 1.7 Hz, 1H), 7.42 (m, 3H), 7.05– 7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, —OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p) ; IR (CHCl$_3$, cm$^{-1}$) 2965, 1727, 1603, 1496, 1458, 1306, 1112. Analysis for C$_{34}$H$_{35}$O$_6$F: Calc: C, 73.10; H, 6.31; Found: C, 73.17; H, 6.42.

C. Preparation of 2-[2-propyl-3-[3-[2-ethyl-4-(4-fluorophenyl)-5-hydroxyphenoxy]propoxy]phenoxy]benzoic acid sodium salt.

2-[2-Propyl-3-[3-[2-ethyl-4-(4-fluorophenyl)-5-hydroxyphenoxy]propoxy]phenoxy]benzoic acid methyl ester (21.5 g, 38.5 mmoles) was hydrolyzed as described above for the preparation of Example 7. The acid was converted to the sodium salt and purified as described in Example 7 to provide 16.7 g (77%) of the desired title product as a white amorphous solid: NMR (DMSO-d$_6$) 10.50 (bs, 1H, —OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9 Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112. Analysis for C$_{33}$H$_{32}$O$_6$FNa: Calc: C, 69.95; H, 5.69; F, 3.35; Found: C, 69.97; H, 5.99; F, 3.52.

EXAMPLE 9

3-(2-(4-(2-Ethyl-4-(4-fluorophenyl)-5-hydroxyphenoxy)butyloxy)phenyl)propionic acid

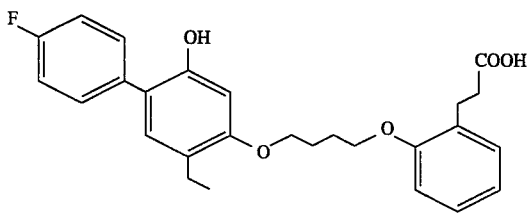

A solution of 375 mg of ethyl 3-(2-(4-(2-ethyl-4-(4-fluorophenyl)-5-hydroxyphenoxy)butyloxy)phenyl)propionate in 25 ml of ethanol was mixed with 5 ml of 5.0N sodium hydroxide and stirred 16 hours. The mixture was diluted with 1.0N hydrochloric acid and extracted with 3:1 dichloromethane/isopropanol. The organic phase was washed with saturated sodium chloride, dried over sodium sulfate, and evaporated in vacuo providing the desired title product in 72% yield. NMR.

EXAMPLE 10

Preparation of 1-[5-ethyl-2-hydroxy-4-[[6-methyl-6-(1H-tetrazol-5-yl)heptyl]oxy]phenyl]ethanone

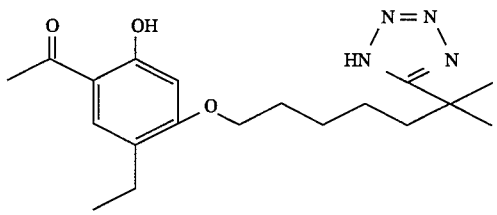

The title compound was prepared as described in U.S. Pat. No. 4,945,099, issued Jul. 31, 1990, which is herein incorporated by reference.

EXAMPLE 11

Preparation of 2,4-diethyl-5-[[6-methyl-6-(1H-tetrazol-5-yl)heptyl]oxy]phenol

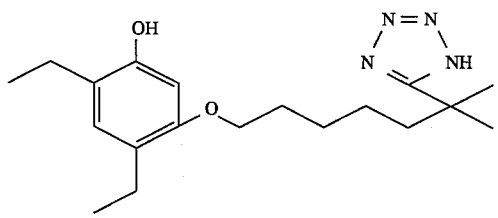

The title compound was prepared as described in U.S. Pat. No. 4,945,099, issued Jul. 31, 1990, which is herein incorporated by reference.

EXAMPLE 12

Preparation of 3,4-dihydro-8-propyl-7-[3-(2-ethyl-5-hydroxy-4-ethoxy-phenoxy)propoxy]-2H-1-benzopyran-2-carboxylic acid

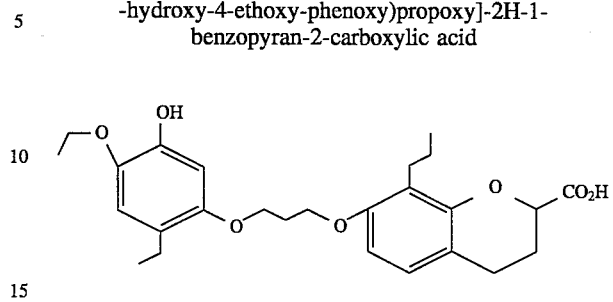

A. Preparation of 5-Ethyl-2,4-Dihydroxybenzaldehyde.

Dimethyformamide (250 ml) was cooled to 0° C. under argon atmosphere. With stirring, phosphorous oxychloride (18.60 ml, 0.20 mole) was added slowly to the N,N-dimethylformamide. After several minutes at 0° C., the reaction was warmed to room temperature and methylene chloride (150 ml) was added to the reaction mixture to dissolve the solid. The reaction was subsequently recooled to 0° C. 4-Ethylresorcinol (25.0 g, 0.181 mole) was added to the reaction mixture as a 200 ml methylene chloride solution. After stirring at 0° C. for 10 minutes., the reaction was warmed to room temperature and then refluxed for 16 h. The reaction was cooled to room temperature, and a 100 ml water solution of sodium acetate (50 g) was added slowly. This mixture was refluxed for 40 minutes then cooled to room temperature. The aqueous layer was washed several times with methylene chloride. The organics were combined and washed with 1N hydrochloric acid solution and brine the dried over magnesium sulfate. Filtration and solvent removal gave an orange solid which was recrystallized from toluene and hexane (17 g, 56%)

TLC Rf=0.39 (30% EtOAc/Hexane) $^1$HNMR(CDCl$_3$) δ11.30(s,1), 9.71(s,1), 7.29(s,1), 6.36(s(br),1), 2.61(q,2,J=7.48 Hz), 1.25(t,3,J=7.54 Hz)

B. Preparation of 1-(3-chloropropoxy-1-yl)-3-hydroxy-4-formyl-5-ethyl benzene.

A 190 ml dry tetrahydrofuran solution of 5-ethyl-2,4-dihydroxybenzaldehyde (8.00 g, 48.1 moles), 3-chloropropanol (4.55 g, 48.1 moles) and triphenylphosphine (12.62 g, 48.1 mmoles) were stirred at room temperature. To this solution was added a 10 ml tetrahydrofuran solution of diethyl azodicarboxylate (7.60 ml, 48.1 mmoles). The reaction was stirred at room temperature for 17 h after which the solvent was removed under vacuum. The crude material was adsorbed onto 125 g of 60 micron silica gel and then eluted through a plug 100 ml plug of silica gel with 1 L of 30% ethyl acetate/hexane. The resulting yellow oil was then further purified by Waters Prep 500 chromatography on silica gel eluting with a solvent gradient of 5% to 30% ethyl acetate/hexane over 45 minutes. The desired product was obtained as a clear oil (7.03 g, 61%).

TLC Rf=0.47 (30% EtOAc/Hexane) $^1$HNMR(CDCl$_3$) δ11.40(s,1), 9.71(s,1), 7.26(s,1), 6.42(s,1), 4.18(t,2,J=5.80 Hz), 3.77(t,2,J=6.28 Hz), 2.57(q,2,J=7.41 Hz), 2.30(m,2), 1.96(t,3,J=7.54 Hz) IR(CHCl$_3$) 3021, 2971, 2937, 1643, 1586, 1494 cm$^{-1}$ Mass Spec(FD) m/e 243 (M$^+$) Analysis for C$_{12}$H$_{15}$O$_3$Cl Theory: C, 59.33; H, 6.23; Cl, 14.61 Found C, 59.24; H, 6.18; Cl, 14.69

C. Preparation of 1-Benzyloxy-3-[3-chloropropoxy]-4-ethyl-6-formyl benzene.

A suspension of hexane washed sodium hydride (2.40 g of 60% oil dispersion, 60 mmoles) in dry N,N-dimethylformamide was stirred under argon atmosphere at room temperature. A 50 ml dry N,N-dimethylformamide solution of 1-(3-chloropropoxy-1-yl)-3-hydroxy-4-formyl-5-ethyl benzene (6.92 g, 28.6 mmoles) was added slowly to the NaH suspension, and this mixture was stirred for 30 minutes at room temperature. Benzyl bromide (9.78 g, 57.2 mmoles) was added to the alkoxide solution and stirring was continued at room temperature. After three hours the reaction was carefully quenched with saturated NH$_4$Cl solution and then the reaction was diluted with water and extracted several times with ethyl acetate. The organic extract was washed with water and dried over magnesium sulfate. Filtration and solvent removal gave a yellow solid. The solid was purified by Waters Prep 500 chromatography using a silica gel support and eluting with a solvent gradient of 5% to 40% ethyl acetate/hexane over a 45 minute period. The desired product was obtained as a white solid (7.14 g, 75%).

TLC Rf=0.34 (30% EtOAc/Hexane) $^1$HNMR(CDCl$_3$) δ10.41(s,1), 7.68(s,1), 7.42(m,5), 6.49(s,1), 5.20(s,2), 4.17(t,2,J=5.78 Hz), 3.78(t,2,J=6.22 Hz), 2.57(q,2,J=7.53 Hz), 2.29(m,2), 1.18(t,3,J=7.50 Hz) IR(CHCl$_3$) 3013, 2971, 2875, 1667, 1607, 1505, 1465 cm$^{-1}$ Mass Spec(FD) m/e 332(M$^+$) Analysis for C$_{19}$H$_{21}$O$_3$Cl: Theory C, 68.57; H, 6.36; Cl, 10,65. Found C, 68.68; H, 6.54; Cl, 10,53.

D. Preparation of 1-Benzyloxy-3-[3-chloropropoxy]-4-ethyl-6-hydroxybenzene.

A solution of the aldehyde prepared supra in methylene chloride (0.18M) at room temperature was treated with m-chloroperbenzoic acid (1.1 eqv), and the reaction was stirred at room temperature. After 30 minutes. a precipitate formed. The reaction was complete after 5 hours. The precipitate was removed by filtration. The solvent was removed under vacuum and the resulting solid was dissolved in tetrahydrofuran (0.28M) and stirred overnight with 2N sodium hydroxide (2.5 eqv).

Subsequently, the tetrahydrofuran was removed under vacuum, and the resulting aqueous mixture was diluted with water and acidified to pH 1 with 1N hydrochloric acid. The milky suspension was extracted several times with ethyl acetate. The organic extract was washed several times with saturated aqueous NaHCO$_3$ solution and then with brine. The organic layer was dried over magnesium sulfate. Filtration and solvent removal gave 8.70 g of a brown oil. The oil was purified by silica gel chromatography.

1-Benzyloxy-2-[3-chloropropoxy]-4-ethyl-6-hyroxybenzene was obtained in 66% yield from 1-Benzyloxy-2-[3-chloropropoxy]-4-ethyl-6-formylbenzene. TLC Rf=0.46 (30% EtOAc/Hexane) $^1$HNMR(CDCl$_3$) δ7.44(m,5), 6.79(s, 1), 6.58(s,1), 5.25(s,1), 5.10(s,2), 4.03(t,2,J=5.77 Hz), 3.78(t,3,J=6.36 Hz), 2.56(q,2,J=7.56 Hz), 2.23(m,2), 1.17(t, 3,J=7.59 Hz). IR(CHCl$_3$) 3552, 3012, 2969, 2934, 1511, 1469 cm$^{-1}$ Mass Spec(FAB) m/e 320(M$^+$) Analysis for C$_{18}$H$_{21}$O$_3$Cl Theory: C, 67.39; H, 6.60; Cl, 11.05. Found: C, 67.09; H, 6.56; Cl, 10.82.

E. Preparation of 1-Benzyloxy-3-[3-chloropropoxy]-4-ethyl-6-ethoxy benzene.

A suspension of hexane washed sodium hydride (2.10 eqv) in dry N,N-dimethylformamide (1.3M solution) was stirred under argon atmosphere at room temperature. A solution of the phenol in dry N,N-dimethylformamide (0.15M) was added slowly to the sodium hydride suspension. The reaction was stirred at room temperature for 30 minutes. 18-Crown-6 was added to the reaction followed by the dropwise addition of alkyl halide (5.0 eqv). After stirring at room temperature for several hours the reaction was quenched with saturated aqueous ammonium chloride solution, diluted with water and extracted with ethyl acetate. The ethyl acetate extract was washed with water and then dried over magnesium sulfate. Filtration and solvent gave the crude product which was purified by silica gel flash chromatography.

1-Benzyloxy-2-[3-chloropropoxy]-4-ethyl-6-ethoxy benzene was prepared in 77% yield as a white solid from 1-Benzyloxy-2-[3-chloropropoxy]-4-ethyl-6-hydroxy benzene and ethyliodide.

TLC Rf=0.48 (30% EtOAc/Hexane) $^1$HNMR(CDCl$_3$) δ7.40(m,5), 6.80(s,1), 6.56(s,1), 5.16(s,2), 4.10(q,2,J=6.97 Hz), 4.00(t,2,J=5.70 Hz), 3.77(t, z, J=6.73 Hz), 2.60(q,2,J=7.50 Hz), 2.21(m,2), 1.43(t,3,J=6.97 Hz), 1.20(t,3,J=7.46 Hz) IR(CHCl$_3$) 3011, 2971, 2950, 2890, 1620, 1507, 1471 cm$^{-1}$ Mass Spec(FAB) m/e 348(M$^+$) Analysis for C$_{20}$H$_{25}$O$_3$Cl Theory: C,68.86; H,7.22 Found: C,69.35; H,7.38

F. Preparation of Chromone

To a solution of 225 ml of absolute ethanol under argon atmosphere and at room temperature was added 16.56 g of sodium metal over a 1 h. period. After all of the sodium metal was added the reaction mixture was refluxed for 1 hour, then cooled to room temperature. A mixture of 2,4-dihydroxyacetophenone (34.82 g, 0.180 mole), diethyloxylate (54.57 ml, 0.41 mole), absolute ethanol (45 ml), and diethylether (45 ml) was added to the sodium ethoxide solution over 25 minutes. The resulting deep maroon reaction mixture was then refluxed for 2.5 hours and then cooled to room temperature. The reaction mixture was poured into approximately 600 ml of 1N hydrochloric acid and then extracted several times with diethyl ether. The ether was removed from the extract and the resulting gum was dissolved in 135 ml of ethanol. To this solution was then added 2.25 ml of concentrated hydrochloric acid and subsequently refluxed for 45 minutes. The reaction was cooled to room temperature and the ethanol was removed under reduced pressure leaving a brown solid. This solid was dissolved in ethyl acetate and washed once with water, twice with saturated NaHCO$_3$, 1× with water and then dried over magnesium sulfate. Filtration and solvent removal gave 87 g of a brown solid which was recrystallized from ethyl acetate/petroleum ether. Recrystallization provided 24.07 g (48%) of a tan solid chromone.

TLC: Rf=0.27 (40% EtOAc/Hexane). $^1$H NMR (CDCl$_3$) δ8.80 (s(br), 1), 7.98 (d, 1, J=8.78 Hz), 7.13 (d, 1, J=8.78 Hz), 7.13(s, 1), 4.47 (q, 2, J=7.11 Hz), 2.96 (t, 2, J=7.25 Hz), 1.73 (m, 2), 1.46 (t, 3, J=7.16 Hz), 1.02 (t, 3, J=7.11 Hz).

G. Preparation of Ethyl 3,4-dihydro-8-propyl-2H-1-benzopyran-2-carboxylate.

In a Parr bottle, chromone (12.07 g, 0.044 mole) was dissolved in 210 ml of acetic acid. A catalyst (10% palladium/activated carbon) (7.2 g) was added to this solution and the bottle was pressurized with 52 psi of hydrogen gas. The reaction was agitated for 23 hours. The catalyst was removed by filtration through a Celite® pad in a sintered glass funnel. The catalyst was washed with ethyl acetate. The solvent was removed from the filtrate and the resulting oil was azeotroped with toluene providing 12 g of brown oil. The material was purified on a Waters Prep 500 HPLC, equipped with silica gel cartridges, running a 5% to 40% ethyl acetate/hexane gradient over 50 minutes at a flow rate of 250 ml/min and collecting 500 ml fractions. The purified chroman was obtained as a pink oil (10 g, 86%).

TLC: Rf=0.50 (40% EtOAc/Hexane). $^1$H NMR (CDCl$_3$) δ6.73 (d, 1, J=8.20 Hz), 6.37 (d, 1, J=8.20 Hz), 4.78 (s(br), 1), 4.75 (m, 1), 4.25 (m, 2), 2.68 (m, 4), 2.16 (m, 2), 1.60 (m, 2), 1.29 (t, 3, J=7.07 Hz), 0.99 (t, 3, J=7.34 Hz).

H. Preparation of ethyl [3-[(1-benzyloxy-4-ethyl-2 -ethoxy-5-yl)oxy]propoxy]-3,4-dihydro-8-propyl-2H-1 -benzopyran-2-carboxylate.

To a solution of 1-benzyloxy-3-[3-chloropropoxy]-4-ethyl-6 -ethoxy benzene (1.0 g, 2.87 mmoles) in acetone (8.0 ml) and under argon atmosphere, added sodium iodide (4.31 g, 28.7 mmoles). The reaction mixture was refluxed for 8 h and then cooled to room temperature. The acetone was removed from the reaction mixture under vacuum, and the residue was dissolved in diethylether and washed with water. The ether extract was dried over magnesium sulfate and filtered. Solvent removal gave 1.09 g of the iodide as a yellow oil which solidified on standing at −4° C.

Under argon atmosphere and at room temperature, a mixture of ethyl 3,4-dihydro-8-propyl-2H-1-benzopyran-2-carboxylate (0.545 g, 2.06 mmoles) and potassium carbonate (0.854 g,6.18 mmoles) in 4.0 ml of dry N,N-dimethylformamide was treated with a 4.0 ml N,N-dimethylformamide solution of the above prepared iodide.

After stirring at room temperature for 42 hours the reaction was quenched with water and then extracted several times with ethyl acetate. The ethyl acetate extract was washed with water and then dried over magnesium sulfate. Filtration and solvent removal gave 1.30 g of a yellow oil. The oil was purified by flash chromatography on silica gel eluting with 20% ethyl acetate/hexane. The desired coupled product (0.932 g) was obtained in 79% yield as a yellow oil.

TLC Rf=0.48 (30% EtOAc/Hexane) $^1$HNMR(CDCl$_3$) δ7.43(m,5), 6.85(d,1,J=8.37 Hz), 6.82(s,1), 6.60(s,1), 6.50(d,1,J=8.37 Hz), 5.13(s,2), 4.78(m,1), 4.26(m,2), 4.13(m, 6), 2.67(m,6), 2.24(m,4), 1.62(m,2), 1.46(t,3,J=7.00 Hz), 1.32(t,3, J=7.09 Hz), 1.21(t,3,J=7.47 Hz), 0.98(t,3,J= 7.34 Hz) IR(CHCl$_3$) 3027, 3010, 2966, 2930, 2867, 1750, 1611, 1507, 1469 cm$^{-1}$ Mass Spec (FAB) m/e 486 (M$^+$) Analysis for C$_{35}$H$_{44}$O$_7$ Theory: C, 72.89; H,7.69 Found: C, 72.85; H,7.40

I. Preparation of Ethyl [3-[(6-ethyl-4-ethoxy-3 -hydroxy-1-yl)oxy]propoxy]-3,4-dihydro-8-propyl-2H-1 -benzopyran-2-carboxylate.

To a solution of the benzyl ether in ethyl acetate or methanol (0.14M solution) was added 10% palladium/activaed carbon (15% w/w). Hydrogen gas was bubbled through this solution for 15 minutes. The reaction was then stirred at room temperature under an atmosphere of hydrogen. After starting material was consumed, argon was bubbled through the reaction mixture for 15 minutes. The reaction mixture was filtered through a Celite® pad in a sintered glass funnel, and the catalyst was washed with ethyl acetate. The resulting crude product was purified by flash chromatography using silica gel as the solid support and eluting with an ethyl acetate/hexane mixture.

Ethyl [3-[(6-ethyl-4-ethoxy-3-hydroxy-1-yl)oxy]propoxy] -3,4-dihydro-8-propyl-2H-1-benzopyran-2-carboxylate was prepared from ethyl [3-[(1-benzyloxy-4-ethyl-2-ethoxy-5 -yl)oxy]propoxy]-3,4-dihydro-8-propyl-2H-1-benzopyran-2 -carboxylate in 87% yield as a white solid. TLC Rf=0.32 (30% EtOAc/Hexane) $^1$HNMR(CDCl$_3$) δ6.85(d,1,J=8.37 Hz), 6.74(s,1), 6.62(s,1), 6.52(d,1,J=8.37 Hz), 4.79(m,1), 4.19(m,8), 2.68(m,8), 2.26(m,4), 1.62(m,2), 1.45(t,3,J=6.96 Hz), 1.33(t,3,J=7.14 Hz), 1.21(t,3,J=7.54 Hz), 1.00(t,3,J=7.33 Hz) IR(CHCl$_3$) 3540, 3026, 2965, 2934, 2873, 1750, 1611, 1509, 1492 cm$^{-1}$ Mass Spec(FD) m/e 486(H$^+$) Analysis for C$_{28}$H$_{38}$NO$_7$ Theory: C,69.11; H,7.87 Found: C,69.00; H,8.00

J. Preparation of 3,4-dihydro-8-propyl-7-[3-(2 -ethyl-5-hydroxy-4-ethoxy-phenoxy)propoxy]-2H-1-benzopyran-2-carboxylic acid.

The ethyl ester was stirred in dioxane (0.14M solution) at room temperature. This solution was treated with 3.0 eqv of sodium hydroxide (2N aq solution). The reaction was stirred at room temperature for 2.5 hours and then the dioxane was removed under vacuum. The resulting residue was dissolved in water and acidified to pH 1 with 5N hydrochloric acid (a white ppt. forms). The aqueous mixture was extracted several times with ethyl acetate and then dried over magnesium sulfate. Filtration and solvent removal gave the crude product.

3,4-dihydro-8-propyl-7-[3-(2-ethyl-5-hydroxy-4-ethoxyphenoxy)propoxy]-2H-1-benzopyran-2-carboxylic acid was purified by recrystallization from ethyl acetate/hexane. The desired acid was obtained as white crystals (0.436 g, 71%)

TLC Rf=0.49 (6.5/3.4/0.1 EtOAc/Hexane/AcOH) $^1$HNMR(CDCl$_3$) δ6.84(d,1,J=8.44 Hz), 6.69(s,1), 6.56(s,1), 6.50(d,1,J=8.44 Hz), 5.65(s(br),1), 4.77(dd,1,J=7.62, 3.72 Hz), 4.10(m,6), 2.77(m,2), 2.62(m,4), 2.22(m,4), 1.54(m,2), 1.42(t,3,J=6.98 Hz), 1.16(t,3,J=7.48 Hz), 0.94(t,3,J=7.30 Hz) IR(KBr) 3215(br), 2956, 2930, 2870, 1706, 1613, 1589, 1516 cm$^{-1}$ Mass Spec(FD) m/e 458(M$^+$) Analysis for C$_{26}$H$_{34}$O$_7$ Theory: C, 68.10; H,7.47 Found: C, 68.13; H,7.56

EXAMPLE 13

Preparation of 7-[3-(4-acetyl-2-ethyl-5-hydroxyphenoxy)propoxy]-3,4-dihydro-8-propyl-2H-1 -benzopyran-2-carboxylic acid.

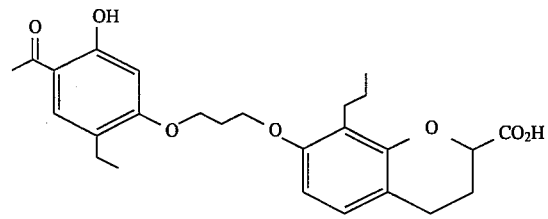

A. Preparation of Chromone.

To a solution of 225 ml of ethanol(Anhydrous) under argon atmosphere. and at room temperature added 16.56 g of Na metal over a 1 hour. period. After all of the Na was added the reaction mixture was refluxed for 1 hour. then cooled to room temperture. A mixture of 2,4-dihydroxyacetophenone (34.82 g, 0.180 mole), diethyloxylate (54.57 ml, 0.41 mole), absolute ethanol (45 ml), and diethylether (45 ml) was added to the sodium ethoxide solution over 25 minutes. The resulting deep maroon reaction mixture was then refluxed for 2.5 hours and then cooled to room temperature. The reaction mixture was poured into approximately 600 ml of 1N hydrochloric acid and then extracted several times with diethyl ether. The ether was removed from the extract and the resulting gum was dissolved in 135 ml of ethanol. To this solution was then added 2.25 ml of concentrated hydrochloric acid and subsequently refluxed for 45 minutes. The reaction was cooled to room temperature and ethanol was removed under reduced pressure leaving a brown solid. This solid was dissolved in ethyl acetate and washed one time with water, two times with saturated sodium bicarbonate, one time with water and then dried over magnesium sulfate. Filtration and solvent removal gave 87 g of a brown solid which was recrystallized from ethyl acetate/petroleum ether. Recrystallization provided 24.07 g (48%) of a tan solid chromone.

TLC: Rf=0.27 (40% EtOAc/Hexane). $^1$H NMR (CDCl$_3$) $\delta$8.80 (s(br), 1), 7.98 (d, 1, J=8.78 Hz), 7.13(d, 1, J=8.78 Hz), 7.13(s, 1), 4.47 (q, 2, J=7.11 Hz), 2.96 (t, 2, J=7.25 Hz), 1.73 (m, 2), 1.46 (t, 3, J=7.16 Hz), 1.02 (t, 3, J=7.11 Hz).

B. Preparation of Ethyl 3,4-dihydro-8-propyl-2H-1-benzopyran-2-carboxylate.

In a pressure bottle, the chromone (12.07 g, 0.044 mole) was dissolved in 210 ml of acetic acid. 10% palladium on activated carbon (7.2 g) catalyst was added to this solution and the bottle was pressurized with 52 psi of H$_2$ gas. The reaction was agitated for 23 hours. The catalyst was removed by filtration through a Celite® pad in a sintered glass funnel. The catalyst was washed with ethyl acetate. The solvent was removed from the filtrate and the resulting oil was azeotroped with toluene providing 12 g of brown oil. The material was purified on a Waters Prep 500 HPLC, equiped with silica gel cartridges, running a 5% to 40% ethyl acetate/hexane gradient over 50 minutes at a flow rate of 250 ml/minutes and collecting 500 ml fractions. The purified chroman was obtained as a pink oil (10 g, 86%).

TLC: Rf=0.50 (40% ethyl acetate/hexane). $^1$H NMR (CDCl$_3$) $\delta$6.73 (d, 1, J=8.20 Hz), 6.37 (d, 1, J=8.20 Hz), 4.78 (s(br), 1), 4.75 (m, 1), 4.25 (m, 2), 2.68 (m, 4), 2.16 (m, 2), 1.60 (m, 2), 1.29 (t, 3, J=7.07 Hz), 0.99 (t, 3, J=7.34 Hz).

C. Ethyl 7-(3-chloropropoxy)-3,4-dihydro-8-propyl-2H-1-benzopyran-2-carboxylate.

A solution (0.3M) of ethyl 3,4-dihydro-8-propyl-2H-1-benzopyran-2-carboxylate in dry N,N-dimethylformamide was stirred under argon atmosphere and at room temperature with solid potassium carbonate (1.75 eqv). To this suspension added 1-bromo-2-chloropropane (2.5 eqv.). The reaction was stirred at room temperature for 20 hours and then quenched with water. The reaction mixture was extracted with ethyl acetate (three times), and the ethyl acetate extract was washed with water and then dried over magnesium sulfate. Filtration and solvent removal gave the crude product as an oil which was purified by flash chromatography on silica gel eluting with 15% ethyl acetate/hexane. Ethyl 7-(3-chloropropoxy)-3,4-dihydro-8-propyl-2H-1-benzopyran-2-carboxylate was prepared in 72% yield.

$^1$H NMR (CDCl$_3$) $\delta$6.83(d,1,J=8.96 Hz), 6.48 (d,1,J=8.96 Hz), 4.77(t, 1, J=5.52 Hz), 4.67(m,2), 4.10 (t,2,J=5.52 Hz), 3.80 (t,2,J=5.50 Hz) 2.70 (m,4), 2.26 (m, 4), 1.6 (m,2),1.28 (t,3,J=7.36 Hz), 0.98 (t,3,J=6.44 Hz) IR (CHCl$_3$) 2963, 2933, 1749, 1728, 1612 cm$^{-1}$ Mass Spec (FAB) (m/z) 341(M$^+$+H), 340(M+)

D. Ethyl 7-[3-(4-acetyl-2-ethyl-5-hydroxyphenoxy)propoxy]-3,4-dihydro-8-propyl-2H-1-benzopyran-2-carboxylate.

To a solution of 2,4-dihydroxy-4-ethyl acetophenone in 5:1 methylethylketone and dimethylsulfoxide (0.45M solution) at room temperature added the chloropropyl ether (1.0 eqv), potassium carbonate (1.75 eqv) and potassium iodide (0.20 eqv). The reaction was then refluxed for 20 hours. The reaction was then cooled to room temperature and quenched with water. The reaction mixture was extracted with ethyl acetate (three times) and this extract was washed with water and then dried over magnesium sulfate. Filtration and solvent removal gave a crude product which was purified by flash chromatography on silica gel eluting with 20% ethyl acetate/hexane. Ethyl 7-[3-(4-acetyl-2-ethyl-5-hydroxyphenoxy)propoxy]-3,4-dihydro-8-propyl-2H-1-benzopyran-2-carboxylate was prepared in 73% yield. $^1$H NMR (CDCl$_3$) $\delta$7.43 (s,1), 6.81 (d,1,J=8.39 Hz),6.47 (d,1,J=8.39 Hz), 6.42 (s,1), 4.75 (m,1), 4.24 (m, 4), 4.14 (t,2,J=5.98 Hz), 2.64 (m, 6), 2.58 (s,3), 2.35 (m,2), 2.20 (m,2), 1.55 (m,2), 1.29 (t,3,J=7.14 Hz), 1.18(t,3,J=7.47 Hz), 0.93(t,3,J=7.34 Hz). IR (CHCl$_3$) 2961, 2931, 2862, 1746, 1715, 1631, 1569 cm$^{-1}$ Mass Spec (FAB) (m/z) 485 (M$^+$+H), 484 (M$^+$) Analysis for C$_{28}$H$_{36}$O$_7$: Theory: C, 69.40; H, 7.49 Found: C, 70.23, H, 8.08

E. 7-[3-(4-acetyl-2-ethyl-5-hydroxyphenoxy)propoxy]-3,4-dihydro-8-propyl-2H-1-benzopyran-2-carboxylic acid.

A solution of ethyl 7-[3-(4-acetyl-2-ethyl-5-hydroxyphenoxy)propoxy]-3,4-dihydro-8-propyl-2H-1-benzopyran-2-carboxylate in dioxane (3.5M solution) was treated with 2N sodium hydroxide (3.0 eqv) and stirred at room temperature. After stirring for 4 hours, the dioxane was removed from the reaction, and the remaining solution was diluted with water and acidified with 5N hydrochloric acid. The resulting milky solution was extracted with ethyl acetate. The ethyl acetate extract was dried over magnesium sulfate and filtered. Solvent removal gave a white solid. The solid was purified by flash chromatography on silica gel eluting with 50% ethyl acetate/hexane, and the resulting solid was crystalized from ethyl acetate and hexane. The desired acid was obtained in 47% yield.

$^1$H NMR (CDCl$_3$) 12.72 (s,1), 7.44 (s,1), 6.86 (d,1,J=8.30 Hz), 6.51 (d,1,J=8.30 Hz), 6.40 (s,1), 4.75 (dd,1,J=9.18 Hz, 4.59 Hz), 4.23(t,2,J=5.74 Hz), 4.15 (t,2,J=5.74 Hz), 2.80 (m,1), 2.62 (m,2), 2.60 (s,3), 2.58 (m,2), 2.35 (m,2), 2.13 (m, 1), 1.55 (m,2), 1.31 (t,3,J=6.90 Hz), 1.20 (t,3,J=8.04 Hz), 0.95 (t,3,J=8.04 Hz) IR (CCl$_4$) 3020, 3000, 2945, 3000, 1775, 1725, 1633, 1615 cm$^{-1}$ Mass Spec (FD) (m/z) 456 (M$^+$) Analysis for C$_{26}$H$_{32}$NO$_7$: Theory: C, 68.40; H, 7.06 Found: C, 68.61; H, 7.22

EXAMPLE 14

Preparation of 2-[3-[3-(4-acetyl-2-ethyl-5-hydroxyphenoxy)propoxy)-2-propylphenoxy]butanoic acid.

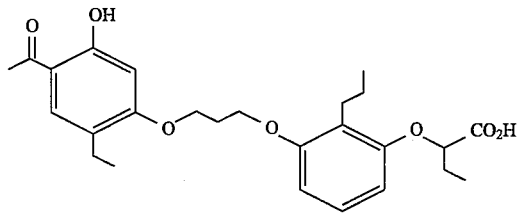

A. Ethyl 2-[2-propyl-3-hydroxyphenoxy]butyrate.

Sodium hydride (0.97 g of a 60% oil dispersion, 24 mmoles) under argon atmosphere was washed with 15 ml of dry hexane. The hexane supernatant was removed via syringe. Dry tetrahydrofuran (40 ml) was added to the sodium hydride and with stirring at room temperature, the dihydroxypropylbenzene (3.68 g, 24 mmoles) was added as a 40 ml tetrahydrofuran solution. After stirring at room temperature for 25 minutes, the ethyl 2-bromo-proprinate (4.48 g, 23 mmoles) was added rapidly. After stirring at room temperature for 17 hours, the reaction was quenched with saturated aqueous ammonium chloride solution, and the tetrahydrofuran was removed under vacuum. The resulting aqueous mixture was extracted several times with ethyl acetate. The organic extract was dried over magnesium sulfate. Filtration and solvent removal gave an orange oil. This oil was purified by Waters Prep 500 chromatography on silica gel eluting with 5 to 30% ethyl acetate/hexane gradient. The desired product was obtained as a clear oil (2.10 g, 33%).

TLC Rf=0.39 (30% EtOAc/Hexane, Silica gel) $^1$H NMR (CDCl$_3$) δ6.96 (t,1,J=8.2 Hz), 6.45 (d,1,J=8.12 Hz), 6.28 (d,1,J=8.12 Hz), 4.88 (s,1), 4.59 (t,l,J=6.04 Hz), 4.20 (q,2, J=7.52 Hz), 2.69 (m,2), 2.02 (m,2), 1.63 (m,2), 1.24 (t,3,J= 7.03 Hz), 1.10 (t,3,J=7.43 Hz), 0.99 (t,3,J=7.40 Hz) IR (CHCl$_3$) 3603, 3009, 2966, 2936, 2873, 1748, 1728, 1596 cm$^{-1}$ Mass Spec (FAB) (m/z) 267 (M$^+$+H), 266(M$^+$)

B. Ethyl 2-[2-propyl-3-(3-chloropropyloxy)phenoxy]butyrate.

A solution (0.3M) of ethyl 2[2-propyl-3-hydroxyphenoxy]butyrate in dry N,N-dimethylformamide was stirred under argon atmosphere and at room temperature with solid potassium carbonate (1.75 eqv). To this suspension added 1-bromo-2-chloropropane (2.5 eqv.). The reaction was stirred at room temperature for 20 hours and then quenched with water. The reaction mixture was extracted with ethyl acetate (three times), and the ethyl acetate extract was washed with water and then dried over magnesium sulfate. Filtration and solvent removal gave the crude product as an oil which was purified by flash chromatography on silica gel eluting with 15% ethyl acetate/hexane. Ethyl 2-[2 -propyl-3-(3-chloropropyloxy)-phenoxy]butyrate was prepared in 85% yield.

$^1$H NMR (CDCl$_3$) δ7.05(t,1,J=8.26 Hz), 6.55 (d,1,J=8.18 Hz), 6.35(d,1,J=8.27 Hz), 4.60 (t,1,J=6.02 Hz), 4.20 (q,2,J= 7.13 Hz), 4.11 (t,2,J=5.75 Hz), 3.79 (t,2,J=6.36 Hz),2.72 (m,2), 2.26 (m,2), 2.01 (m,2), 1.59 (m,2), 1.25 (t,3,J=7.18 Hz), 1.11 (t,3,J=7.39 Hz), 0.97(t,3,J=7.35 Hz) IR (CHCl$_3$) 3020, 2967, 2935, 2872, 1749, 1727, 1594 cm$^{-1}$ Mass Spec (FAB)(m/z) 343 (M$^+$+H), 342(M+) Analysis for C$_{18}$H$_{27}$O$_4$Cl: Theory: C, 63.06; H, 7.94; Cl, 10.34. Found: C, 63.19; H, 7.84; Cl, 10.58.

C. Ethyl 2-[3-[3-(4-acetyl-2-ethyl-5-hydroxyphenoxy)propoxy)- 2-propylphenoxy]butanoate.

To a solution of 2,4-dihydroxy-4-ethyl acetophenone in 5:1 methylethylketone and dimethylsulfoxide (0.45M solution) at room temperature was added ethyl 2-[2 -propyl-3-(3-chloropropyloxy)-phenoxy]butyrate (1.0 eqv), potassium carbonate (1.75 eqv) and potassium iodide (0.20 eqv). The reaction was then refluxed for 20 hours. The reaction was then cooled to room temperature and quenched with water. The reaction mixture was extracted with ethyl acetate (three times) and this extract was washed with water and then dried over magnesium sulfate. Filtration and solvent removal gave a crude product which was purified by flash chromatography on silica gel eluting with 20% ethyl acetate/hexane. Ethyl 2-[3-[3-(4-acetyl-2-ethyl-5 -hydroxyphenoxy)propoxy)-2-propylphenoxy]butanoate was prepared in 78% yield.

$^1$H NMR (CDCl$_3$) δ12.72 (s,1), 7.43(s,1), 7.04 (t,1,J=8.29 Hz), 6.55 (d,1,J=8.30 Hz), 6.42 (s,1), 6.34 (d, 1,J=8.30 Hz), 4.58 (t,1,J=5.98 Hz), 4.20 (m,6), 2.72 (m,2), 2.57 (s,3), 2.56 (m,2), 2.32 (m,2), 2.01 (m,2), 1.53 (m,2), 1.23 (t,3,J=7.06 Hz), 1.18 (t,3,J=7.45 Hz), 1.10 (t,3,J=7.38 Hz), 0.94 (t,3,J= 7.33 Hz). IR (CHCl$_3$) 2969, 2931, 1754, 1730, 1633, 1595 cm$^{-1}$ Mass Spec (FD) (m/z) 486(M$^+$) Analysis for C$_{28}$H$_{38}$O$_7$: Theory: C, 69.11; H, 7.87 Found: C, 69.08, H, 8.05

D. 2-[3-[3-(4-acetyl-2-ethyl-5-hydroxyphenoxy)propoxy)-2 -propylphenoxy]butanoic acid.

A solution of ethyl 2-[2-propyl-3-[[3-(4-acetyl-2-ethyl-5-hydroxy-phenoxy)propyl]oxy]phenoxy]butanoate in dioxane (3.5M solution) was treated with 2N sodium hydroxide (3.0 eqv) and stirred at room temperature. After stirring for 4 hours, the dioxane was removed from the reaction, and the remaining solution was diluted with water and acidified with 5N hydrochloric acid. The resulting milky solution was extracted with ethyl acetate. The ethyl acetate extract was dried over magnesium sulfate and filtered. Solvent removal gave a white solid. The solid was purified by crystalization from diethylether and hexane. The desired acid was obtained in 69% yield.

$^1$H NMR (CDCl$_3$) δ12.72 (s,1), 7.43 (s,1), 7.07 (t,1,J= 8.28 Hz), 6.58 (d,1,J=8.28 Hz), 6.48 (s,1), 6.38 (d,1,J=8.28 Hz), 4.63 (t,1,J=5.98 Hz), 4.23 (t,2,J=6.00 Hz), 4.17 (t,2,J= 5.98 Hz), 2.68 (m,2), 2.58 (s,3), 2.56 (m,2), 2.33 (m,2), 2.05 (m,2), 1.54 (m,2), 1.18 (t,3,J=7.42 Hz), 1.12 (t,3,J=7.36 Hz), 0.94 (t,3,J=7.29 Hz) IR (KBr) 2966, 2930, 2871, 1705, 1641, 1593 cm$^{-1}$ Mass Spec (FD) (m/z) 458 (M$^+$) Analysis for C$_{26}$H$_{34}$O$_7$: Theory: C, 68.10; H, 7.47 Found: C, 68.01; H, 7.51

The biological activity of the compounds of Formula I was evaluated employing an in vitro assay measuring the ability of these compounds to inhibit the activity of cytosolic phospholipase A$_2$. The assay was performed essentially as described in R. Kramer, et al., *Journal of Biological Chemistry*, 266:5268–5272 (1991) with the exception that varying amounts of the compound of Formula I were added to the reaction mixture.

The substrate, sonicated liposomes containing 1-palmitoyl-2[$^{14}$C]arachidonoyl-sn-glycero-3-phosphocholine ([$^{14}$C]PC, 55 mCi/mmole from NEN Research Products) and sn-1,2-dioleoylglycerol (DG, Avanti Polar Lipids, Birmingham, Ala.) at a molar ratio of 2:1, was prepared as follows. [$^{14}$C]PC (20 nmol, 1×10$^6$ dpm, 50 μCi/ml in toluene/ethanol) and DG (10 nmol, 100 μg/ml in chloroform) were dried under nitrogen. The lipids were dispersed in 1 ml of 150 mM sodium chloride, 50 mM HEPES, pH 7.5 (assay buffer) by sonication at 4° C. with a Microson™ probesonicator (Heat Systems Ultrasonics) for 4×15 seconds, with 45 second intervals. Bovine serum albumin (essentially fatty acid free, from a 100 mg/ml stock in water, Sigma) was added to a final concentration of 4 mg/ml. Samples to be assayed for cPLA$_2$ activity were incubated with 50 μl liposomes (0.5 nmol [$^{14}$C]PC, 50,000 dpm containing 0.25 nmol of DG) and varying amounts of the compound of Formula I, in a total volume of 0.2 ml of assay buffer containing 1 mM calcium chloride and 1 mM 2-mercaptoethanol. Incubations were carried out at 37° C. for 15 minutes and terminated by adding 2 ml of Dole's reagent (2-propanol/heptane/0.5M sulfuric acid, 40:10:1 containing 10 μg/ml of stearic acid).

After mixing, 1.2 ml of heptane and 1 ml of water were added. The mixtures were briefly vortexed and the upper phase transferred to tubes containing 2 ml of heptane and 150 mg of Bio-Sil (Bio-Rad Laboratories) activated at 130° C. before use. The tubes were thoroughly vortexed and centrifuged (1000×g for 5 minutes). The supernatants were decanted into scintillation vials. After addition of 10 ml of a liquid scintillation cocktail (Ready Protein®, Beckman) radioactivity was counted using a Beckman liquid scintillation counter Model LS 7000. High radioactive counts correlate with enzymatic activity.

Table I, infra, depicts the results of one such series of experiments. The first column provides the example number of the test inhibitor. The second column provides the concentration of the test compound (in micromolar quantities) which inhibits fifty percent of the activity of cytosolic phospholipase $A_2$.

TABLE I

Inhibition of Cytosolic Phospholipase $A_2$

| Example | Human Cytosolic PLA$_2$ IC$_{50}$ (μM) |
|---|---|
| 2 | 18 |
| 3 | 17 |
| 4 | 39.4 |
| 5 | 12 |
| 6 | 9 |
| 8 | 12 |
| 9 | 35 |
| 10 | 43 |
| 11 | 54 |
| 12 | 28 |
| 13 | 13 |
| 14 | 14 |

Immunocytochemistry

Immunocytochemistry has demonstrated increased numbers of reactive astrocytes containing cytosolic phospholipase $A_2$ in the astrocytes of brains from patients suffering from Alzheimer's disease. Immunochemistry was performed on paraffin sections from human occipital cortex of persons afflicted with Alzheimer's disease as well as normal persons. In each case the tissue was fixed only briefly (60–90 minutes) and then transferred to Tris-buffered saline for several days prior to embedding. The monoclonal antibody M12 was raised against purified cPLA$_2$ from U937 cells using standard techniques. Ascites were produced in BALB/c mice and antibodies were affinity-purified using Protein A Fast Flow™ resin. The antibody M12 recognizes the native form of cPLA$_2$ and is also a neutralizing antibody. A rabbit antiserum to glial fibrillary acidic protein (GFAP; Biogenex Labs, San Ramon, Calif.) was used to label astrocytes.

Immunostaining of tissue sections (10 μM) utilized conventional immunoperoxidase techniques and employed the avidin-biotin peroxidase system (ABC, Vector Laboratories, Burlingame, Calif.). For cPLA$_2$ localization, 0.1 mg/ml M12 antibody was used. Anti-GFAP was obtained as prediluted antisera. Dual localization was carried out by sequential immunostaining. An alkaline phosphatase-streptavidin system (Biogenex Labs) using Fast Red™ as chromogen was used to localize the rabbit antibody (GFAP) and nickel chloride-enhanced DAB (Vector Laboratories) was used to detect the peroxidase-labeled mouse anti-cPLA$_2$.

These immunochemistry studies demonstrated localization of cPLA$_2$ in protoplasmic astrocytes in the gray matter and provide further evidence for the importance of this cell type in inflammatory processes in the brain. Comparison of normal adult brains with those brains from persons afflicted with Alzheimer's disease evinces the role of cytosolic phospholipase $A_2$ in the inflammatory component of this disease.

Since the compounds employed in the present invention are effective inhibitors of cytosolic phospholipase $A_2$, these compounds are of value in the treatment of a wide variety of clinical conditions. This invention provides methods of treating or preventing Alzheimer's disease in a mammal which comprises administering to a mammal in need thereof an effective amount of a compound of Formula I.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way.

In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| 2-[2-Propyl-3-[3-[2-ethyl-4-(4-fluorophenyl)-5-hydroxyphenoxy]propoxy]phenoxy]benzoic acid | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| 3-[5-methoxy-2-(4-(2-ethyl-4-(4-fluorophenyl)-5-hydroxyphenoxy)-butyloxy)phenyl]propionic acid | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| 8-Propyl-7-[3-[4-(4-fluorophenyl)-2-ethyl-5-hydroxyphenoxy]propoxy]-3,4-dihydro-2H-1-benzopyran-2-carboxylic acid | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| 2-phenyl-4-ethyl-5-[[6-(2H-tetrazol-5-yl)-6-methylheptyl]oxy]phenol | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Preparation 5

Capsules, each containing 40 mg of medicament are made as follows:

| Ingredient | Quantity (mg/capsule) |
| --- | --- |
| 3,4-dihydro-8-propyl-7-[3-(2-ethyl-5-hydroxy-4-ethoxy-phenoxy)propoxy]-2H-1-benzopyran-2-carboxylic acid | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 225 mg of active ingredient are made as follows:

| Ingredient | Amount |
| --- | --- |
| 2,4-diethyl-5-[[6-methyl-6-(1H-tetrazol-5-yl)heptyl]oxy]phenol | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| 8-Propyl-7-[3-[4-(4-fluorophenyl)-2-ethyl-5-hydroxyphenoxy]propoxy]-3,4-dihydro-2H-1-benzopyran-2-carboxylic acid, ethyl ester | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| (E)-5-(3-carboxybenzoyl)-2-[[6-(4-methoxyphenyl)-5-hexenyl]oxy]-benzenepropanoic acid | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Preparation 9

An intravenous formulation may be prepared as follows:

| Ingredient | Quantity |
| --- | --- |
| 7-[3-(4-acetyl-2-ethyl-5-hydroxyphenoxy)-propoxy]-3,4-dihydro-8-propyl-2H-1-benzopyran-2-carboxylic acid | 250.0 mg |
| Isotonic saline | 1000 ml |

Formulation Example 10

A topical formulation may be prepared as follows:

| Ingredient | Quantity |
| --- | --- |
| 3,4-dihydro-8-propyl-7-[3-(2-ethyl-5- | 1–10 g |

| Ingredient | Quantity |
| --- | --- |
| hydroxy-4-ethoxy-phenoxy)propoxy]-2H-1-benzopyran-2-carboxylic acid | |
| Emulsifying wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment of Alzheimer's disease in a mammal which comprises administering to a mammal in need of said treatment an effective amount of an inhibitor of phospholipase $A_2$ activity or a pharmaceutically acceptable salt of said inhibitor.

2. A method as claimed claim 1 wherein said inhibitor of phospholipase $A_2$ activity is specific for cytosolic phospholipase $A_2$.

3. A method as claimed in claim 1 employing a compound of the formula

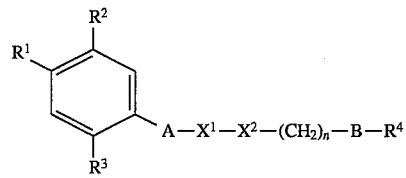

wherein $R^1$ is hydrogen, $C_1$–$C_6$ alkoxycarbonyl, $C_1$–$C_6$ alkoxy, $C_2$–$C_6$ alkanoyl, $C_1$–$C_6$ alkyl, or phenyl, said phenyl being optionally substituted with one or more halo substituents;

$R^2$ is hydroxy, $C_1$–$C_6$ alkoxy, hydrogen, or $C_1$–$C_6$ alkyl;

$R^3$ is $C_1$–$C_6$ alkyl or hydrogen;

A is —O— or —CH$_2$—;

$X^1$ and $X^2$ are each —CH$_2$— or taken together form —CH=CH—;

n is 0 to 6;

B is —O—, —CH$_2$—, or —C($R^5R^6$)—;

where $R^5$ and $R^6$ are independently hydrogen or $C_1$–$C_6$ alkyl;

$R^4$ is phenyl, xanthenyl, tetrazolyl, or 3,4-dihydrobenzopyranyl, said phenyl, xanthenyl, or 3,4-dihydrobenzopyranyl being optionally substituted with one or more substituents selected from the group consisting of $C_1$–$C_6$ alkyl, $C_1$–$C_6$ alkoxy, oxo, carboxy, $C_1$–$C_6$ alkoxycarbonyl, carboxy-($C_1$–$C_6$ alkoxy)-, carboxy-($C_1$–$C_6$ alkyl)-, $NR^7R^8$—C(O)—($C_1$–$C_6$ alkyl)-,

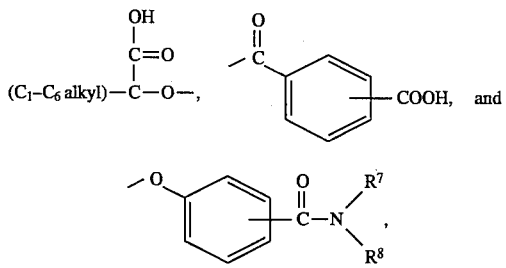

where $R^7$ and $R^8$ are independently hydrogen, $C_1$–$C_6$ alkyl, $C_1$–$C_6$ alkylsulfonyl, or phenylsulfonyl; or a pharmaceutically acceptable salt thereof.

4. A method as claimed in claim 3 employing a compound wherein $R^1$ is optionally substituted phenyl.

5. A method as claimed in claim 3 employing a compound wherein $R^1$ is phenyl substituted with halo.

6. A method as claimed in claim 5 employing a compound selected from the group consisting of N,N-dimethyl- 3-(2-(3-(2-ethyl-4-(4-fluorophenyl)-5 -hydroxyphenoxy)propoxy)phenyl)propionamide, N-methanesulfonyl- 3-(2-(3-(2-ethyl-4-(4-fluorophenyl)-5 -hydroxyphenoxy)propoxy)phenyl)propionamide, N-phenylsulfonyl- 3-(2-(3-(2-ethyl-4-(4-fluorophenyl)-5 -hydroxyphenoxy)propoxy)phenyl)propionamide, 8-propyl-7-[3 -[4-(4-fluorophenyl)-2-ethyl-5-hydroxyphenoxy]propoxy]- 3,4 -dihydro-2H-1-benzopyran-2-carboxylic acid, 2-[2-propyl-3 -[3-[2-ethyl-4-(4-fluorophenyl)-5 -hydroxyphenoxy] propoxy]phenoxy]benzoic acid, and 3-(2-(4 -(2-ethyl-4-(4-fluorophenyl)-5-hydroxyphenoxy)butyloxy)phenyl)propionic acid or a pharmaceutically acceptable salt of any of these compounds.

7. A method as claimed in claim 3 employing a compound wherein $R^1$ is $C_2$–$C_6$ alkanoyl.

8. A method as claimed in claim 7 employing 2 -[3-[3-(4-acetyl-2-ethyl-5-hydroxyphenoxy)-propoxy)-2 -propylphenoxy]butanoic acid or 7-[3-(4-acetyl-2-ethyl-5 -hydroxyphenoxy)propoxy]-3,4-dihydro-8-propyl-2H -1 -benzopyran-2-carboxylic acid or a pharmaceutically acceptable salt of any of these compounds.

9. A method as claimed in claim 3 employing a compound wherein $R^4$ is tetrazolyl.

10. A method as claimed in claim 9 employing a compound wherein $R^2$ is hydroxy.

11. A method as claimed in claim 10 employing 2 -phenyl-4-ethyl-5-[[6-(2H-tetrazol-5-yl)-6 -methylheptyl]oxy]phenol, 1-[5-ethyl-2-hydroxy-4-[[6-methyl-6-(1H-tetrazol-5-yl)heptyl]oxy]phenyl]ethanone, or 2,4 -diethyl-5-[[6-methyl-6-(1H-tetrazol-5-yl)heptyl]oxy]phenol or a pharmaceutically acceptable salt of any of these compounds.

12. A method as claimed in claim 3 employing 2 -[3-[3-[(5-ethyl-2-hydroxy[1,1'-biphenyl]-4-yl)oxy]propoxy] -2-propylphenoxy]propanoic acid, 7-carboxy-9-oxo-3-[3-(2 -ethyl-5-hydroxy-4-phenylphenoxy)propoxy]-9H-xanthene-4 -propanoic acid, or 3,4-dihydro-8-propyl-7-[3-(2-ethyl-5 -hydroxy-4-ethoxy-phenoxy)propoxy]-2H -1-benzopyran-2 -carboxylic acid or a pharmaceutically acceptable salt of any of these compounds.

* * * * *